(12) United States Patent
Claessen et al.

(10) Patent No.: US 11,455,774 B2
(45) Date of Patent: Sep. 27, 2022

(54) AUTOMATED 3D ROOT SHAPE PREDICTION USING DEEP LEARNING METHODS

(71) Applicant: PROMATON HOLDING B.V., The Hague (NL)

(72) Inventors: Frank Theodorus Catharina Claessen, Amsterdam (NL); Bas Alexander Verheij, Amsterdam (NL); David Anssari Moin, Amsterdam (NL); Teo Cherici, Leiden (NL)

(73) Assignee: PROMATON HOLDING B.V., Amsterdam (NL)

( * ) Notice: Subject to any disclaimer, the term of this patent is extended or adjusted under 35 U.S.C. 154(b) by 0 days.

(21) Appl. No.: 16/956,333

(22) PCT Filed: Dec. 21, 2018

(86) PCT No.: PCT/EP2018/086686
§ 371 (c)(1),
(2) Date: Jun. 19, 2020

(87) PCT Pub. No.: WO2019/122373
PCT Pub. Date: Jun. 27, 2019

(65) Prior Publication Data
US 2021/0082184 A1  Mar. 18, 2021

(30) Foreign Application Priority Data
Dec. 22, 2017  (EP) .................................. 17210529

(51) Int. Cl.
*G06T 15/00*  (2011.01)
*G06T 17/20*  (2006.01)
(Continued)

(52) U.S. Cl.
CPC ................ *G06T 17/20* (2013.01); *A61B 6/14* (2013.01); *A61C 9/0053* (2013.01);
(Continued)

(58) Field of Classification Search
CPC ................... G06T 7/11; G06T 2210/41; G06T 2207/20084; G06T 2200/08;
(Continued)

(56) References Cited

U.S. PATENT DOCUMENTS

| | | | |
|---|---|---|---|
| 6,721,387 B1 | 4/2004 | Naidu et al. | |
| 8,135,569 B2 | 3/2012 | Matov et al. | |

(Continued)

FOREIGN PATENT DOCUMENTS

| | | |
|---|---|---|
| CN | 101977564 A | 2/2011 |
| CN | 106618760 A | 5/2017 |

(Continued)

OTHER PUBLICATIONS

Zhou X, Gan Y, Xiong J, Zhang D, Zhao Q, Xia Z. A method for tooth model reconstruction based on integration of multimodal images. Journal of healthcare engineering. Jun. 20, 2018;2018.*

(Continued)

*Primary Examiner* — Phu K Nguyen
(74) *Attorney, Agent, or Firm* — Steven M. Koehler; Westman, Champlin & Koehler, P.A.

(57) ABSTRACT

A computer-implemented method for automated 3D root shape prediction comprising: receiving data defining at least one 3D representation of a tooth and processing the data including: transforming at least part of the data into a voxel representation of a crown; a pre-processor providing the representation of the crown to the input of the neural network trained on clinical representations of real teeth; the first neural network generating a representation of a root or a tooth from the crown, wherein the generation of the (Continued)

representation of the root or tooth includes: determining voxel activations in a voxel space of the output of the deep learning network, each activation representing a probability measure defining the probability that a voxel is part of the root or the tooth; and, determining whether a voxel activation is part of the root or the tooth by comparing the voxel activation with a voxel activation threshold value.

20 Claims, 20 Drawing Sheets

(51) Int. Cl.
    *G06T 7/11*     (2017.01)
    *A61B 6/14*     (2006.01)
    *A61C 9/00*     (2006.01)
    *G06N 3/04*     (2006.01)
    *G06N 3/08*     (2006.01)
    *A61B 6/03*     (2006.01)
    *A61B 6/00*     (2006.01)

(52) U.S. Cl.
    CPC ............ *G06N 3/0454* (2013.01); *G06N 3/08* (2013.01); *G06T 7/11* (2017.01); *A61B 6/032* (2013.01); *A61B 6/4085* (2013.01); *G06T 2200/08* (2013.01); *G06T 2207/10081* (2013.01); *G06T 2207/10116* (2013.01); *G06T 2207/20081* (2013.01); *G06T 2207/20084* (2013.01); *G06T 2210/41* (2013.01)

(58) Field of Classification Search
    CPC ........... G06T 2207/10116; G06T 17/00; G06T 2207/10081; G06T 17/20; G06T 2207/20081; A61C 9/0046; A61C 9/0053; A61B 6/032; A61B 6/4085; A61B 6/14; G06N 3/08; G06N 3/0454
    USPC ........................................................ 345/418
    See application file for complete search history.

(56) References Cited

U.S. PATENT DOCUMENTS

| | | | |
|---|---|---|---|
| 8,439,672 B2 | 5/2013 | Matov et al. | |
| 8,639,477 B2 | 1/2014 | Chelnokov et al. | |
| 9,107,722 B2 | 8/2015 | Matov et al. | |
| 9,135,498 B2 | 9/2015 | Andreiko et al. | |
| 9,904,999 B2 | 2/2018 | Andreiko et al. | |
| 10,032,271 B2 | 7/2018 | Somasundaram et al. | |
| 10,235,606 B2 | 3/2019 | Miao et al. | |
| 10,456,229 B2 | 10/2019 | Fisker et al. | |
| 10,610,185 B2 | 4/2020 | Taguchi et al. | |
| 10,685,259 B2 * | 6/2020 | Salah | G06K 9/6215 |
| 10,932,890 B1 * | 3/2021 | Sant | G16H 40/67 |
| 10,997,727 B2 * | 5/2021 | Xue | G06K 9/6209 |
| 11,007,036 B2 * | 5/2021 | Pokotilov | A61C 7/002 |
| 11,107,218 B2 * | 8/2021 | Salah | G06T 7/0014 |
| 2008/0253635 A1 | 10/2008 | Spies et al. | |
| 2009/0191503 A1 | 7/2009 | Matov et al. | |
| 2010/0069741 A1 | 3/2010 | Kuhn et al. | |
| 2011/0038516 A1 | 2/2011 | Koehler et al. | |
| 2011/0081071 A1 | 4/2011 | Benson et al. | |
| 2011/0255765 A1 | 10/2011 | Carlson et al. | |
| 2013/0039556 A1 | 2/2013 | Kachelriess et al. | |
| 2013/0230818 A1 | 9/2013 | Matov et al. | |
| 2014/0169648 A1 | 6/2014 | Andreiko et al. | |
| 2014/0227655 A1 | 8/2014 | Andreiko et al. | |
| 2015/0029178 A1 | 1/2015 | Claus et al. | |
| 2016/0008095 A1 | 1/2016 | Matov et al. | |
| 2016/0042509 A1 | 2/2016 | Andreiko et al. | |
| 2016/0078647 A1 | 3/2016 | Schildkraut et al. | |
| 2016/0117850 A1 | 4/2016 | Jin et al. | |
| 2016/0324499 A1 | 11/2016 | Sen Sharma et al. | |
| 2016/0371862 A1 | 12/2016 | Silver et al. | |
| 2017/0024634 A1 | 1/2017 | Miao et al. | |
| 2017/0046616 A1 | 2/2017 | Socher et al. | |
| 2017/0100212 A1 | 4/2017 | Sherwood et al. | |
| 2017/0150937 A1 | 6/2017 | Stille et al. | |
| 2017/0169562 A1 | 6/2017 | Somasundaram et al. | |
| 2017/0265977 A1 | 9/2017 | Fisker et al. | |
| 2017/0270687 A1 | 9/2017 | Manhart | |
| 2018/0028294 A1 | 2/2018 | Azernikov et al. | |
| 2018/0182098 A1 | 4/2018 | Maraj et al. | |
| 2018/0300877 A1 | 10/2018 | Somasundaram et al. | |
| 2019/0026599 A1 * | 1/2019 | Salah | G06K 9/6273 |
| 2019/0147666 A1 | 5/2019 | Keustermans et al. | |
| 2019/0164288 A1 | 5/2019 | Wang et al. | |
| 2019/0172200 A1 | 6/2019 | Andreiko et al. | |
| 2019/0282333 A1 | 9/2019 | Matov et al. | |
| 2019/0328489 A1 | 10/2019 | Capron-Richard et al. | |
| 2020/0015948 A1 | 1/2020 | Fisker et al. | |
| 2020/0022790 A1 * | 1/2020 | Fisker | B33Y 10/00 |
| 2020/0085535 A1 * | 3/2020 | Pokotilov | A61C 7/002 |
| 2020/0179089 A1 | 6/2020 | Serval et al. | |
| 2020/0320685 A1 | 10/2020 | Anssari Moin et al. | |
| 2021/0045843 A1 * | 2/2021 | Pokotilov | A61C 7/08 |
| 2021/0110584 A1 | 4/2021 | Claessen et al. | |
| 2021/0150702 A1 | 5/2021 | Claessen et al. | |
| 2021/0174543 A1 | 6/2021 | Claessen et al. | |
| 2021/0217233 A1 * | 7/2021 | Feng | G06T 17/005 |
| 2021/0264611 A1 * | 8/2021 | Xue | G06K 9/4604 |
| 2021/0322136 A1 | 10/2021 | Anssari Moin et al. | |

FOREIGN PATENT DOCUMENTS

| | | |
|---|---|---|
| CN | 108205806 A | 6/2018 |
| CN | 108305684 A | 7/2018 |
| EP | 2742857 A1 | 6/2014 |
| EP | 3121789 A1 | 1/2017 |
| EP | 3462373 A1 | 4/2019 |
| EP | 3591616 A1 | 1/2020 |
| EP | 3671531 A1 | 6/2020 |
| EP | 3767521 A1 | 1/2021 |
| JP | 2013-537445 A | 10/2013 |
| WO | 2015169910 A1 | 11/2015 |
| WO | 2017099990 A1 | 6/2017 |
| WO | 2019002631 A1 | 1/2019 |
| WO | 2019068741 A1 | 4/2019 |
| WO | 2019207144 A1 | 10/2019 |
| WO | 2020007941 A1 | 1/2020 |
| WO | 2020048960 A1 | 3/2020 |
| WO | 2020127398 A1 | 6/2020 |
| WO | 2021009258 A1 | 1/2021 |

OTHER PUBLICATIONS

Görler O, Akkoyun S. Artificial Neural Networks Can be Used as Alternative Method to Estimate Loss Tooth Root Sizes for Prediction of Dental Implants. Fen Bilimleri Dergisi (CFD). Apr. 2017;38(2).*

Johari M, Esmaeili F, Andalib A, Garjani S, Saberkari H. Detection of vertical root fractures in intact and endodontically treated premolar teeth by designing a probabilistic neural network: an ex vivo study. Dentomaxillofacial Radiology. Feb. 2017;46(2): Jan. 7, 2016.*

Eun H, Kim C. Oriented tooth localization for periapical dental X-ray images via convolutional neural network. In2016 Asia-Pacific Signal and Information Processing Association Annual Summit and Conference (APSIPA) Dec. 13, 2016 (pp. 1-7). IEEE.*

Çiçek et al. "3D U-Net: Learning Dense Volumetric Segmentation from Sparse Annotation", Medical Image Computing and Computer-Assisted Intervention—MICCAI 2016, Part II, Oct. 2, 2016, pp. 424-432.

Gkantidis et al. "Evaluation of 3-Dimensional Superimposition Techniques on Various Skeletal Structures of the Head Using Surface Models", PLoS One, Feb. 23, 2015, 20 pages, vol. 10, No. 2.

Gjesteby et al. "Deep Learning Methods for CT Image-Domain Metal Artifact Reduction", SPIE, Developments in X-Ray Tomography XI, Sep. 25, 2017, 6 pages, vol. 10391.

(56) References Cited

OTHER PUBLICATIONS

Hall, P. and Owen, M. "Simple Canonical Views", Proceedings of the British Machine Vision Conference (BMVC), Sep. 2005, 10 pages.

Han et al. "Deep Residual Learning for Compressed Sensing CT Reconstruction Via Persistent Homology Analysis", Cornell University Library, Nov. 19, 2016, pp. 1-10.

Hongming Li, Y. "Non-Rigid Image Registration Using Fully Convolutional Networks With Deep Self-Supervision", Sep. 3, 2017, 8 pages.

Isola et al. "Image-to-Image Translation with Conditional Adversarial Networks", 2017 IEEE Conference on Computer Vision and Pattern Recognition (CVPR), Honolulu, HI, 2017, pp. 5967-5976.

Joda, T. and Gallucci, G. "Systematic Literature Review of Digital Three-Dimensional Superimposition Techniques to Create Virtual Dental Patients", The International Journal of Oral & Maxillofacial Implants, 2015, pp. 330-337, vol. 30, No. 2.

Jung et al. "Combining Volumetric Dental CT and Optical Scan Data for Teeth Modeling", Computer-Aided Design, Oct. 2015, pp. 24-37, vol. 67-68.

Li et al. "PointCNN: Convolution On X-Transformed Points", Neural Information Processing Systems (NIPS), Nov. 5, 2018, 11 pages.

Meyer et al. "Normalized Metal Artifact Reduction (NMAR) in Computed Tomography", Medical Physics, Oct. 2010, pp. 5482-5493, vol. 37, No. 10.

Pavaloiu et al. "Automatic Segmentation for 3D Dental Reconstruction", IEEE 6th ICCCNT, Jul. 13-15, 2015, 6 pages.

Pavaloiu et al. "Neural Network Based Edge Detection for CBCT Segmentation", 5th IEEE EHB, Nov. 19-21, 2015.

Qi et al. "PointNet: Deep Learning on Point Sets for 3D Classification and Segmentation", Computer Vision and Pattern Recognition (CVPR), 2017, 19 pages.

Ruellas et al. "3D Mandibular Superimposition: Comparison of Regions of Reference for Voxel-Based Registration" PLoS One, Jun. 23, 2016, 13 pages.

Schulze et al. "Artefacts in CBCT: A Review", Dentomaxillofacial Radiology, Jul. 1, 2011, pp. 265-273, vol. 40, No. 5.

Simonovsky et al. "A Deep Metric for Multimodal Registration" International Conference on Medical Image Computing and Computer-Assisted Intervention (MICCAI), 2016, pp. 10-18, vol. 9902.

Tonioni et al. "Learning to Detect Good 3D Keypoints", International Journal of Computer Vision, 2018, pp. 1-20, vol. 126.

Wang et al. "Dynamic Graph CNN for Learning on Point Clouds", ACM Trans. Graph, Jan. 2019, vol. 1, No. 1, 13 pages.

Wu et al. "Tooth Segmentation on Dental Meshes Using Morphologic Skeleton", Computers & Graphics, Feb. 2014, pp. 199-211, vol. 38.

Yau et al. "Tooth Model Reconstruction Based Upon Data Fusion for Orthodontic Treatment Simulation", Computers in Biology and Medicine, May 1, 2014, pp. 8-16, vol. 48.

Yu, Y. "Machine Learning for Dental Image Analysis", Nov. 2016, 61 pages, https://arxiv.org/ftp/arxiv/papers/1611/1611.09958.pdf, retrieved Nov. 30, 2017.

Zhang, Y. and Yu, H. "Convolutional Neural Network Based Metal Artifact Reduction in X-Ray Computed Tomography", IEEE Transactions on Medical Imaging, Jun. 2018, pp. 1370-1381, vol. 37, No. 6.

Zhang, C. and Xing, Y. "CT Artifact Reduction Via U-Net CNN", SPIE, Medical Imaging 2018: Image Processing, Mar. 2, 2018, 6 pages, vol. 10574.

Liao et al, "Automatic Tooth Segmentation of Dental Mesh Based on Harmonic Fields", Hindawi Publishing Corporation, BioMed Research International, vol. 2015, Article IDS 187173, 10 pages, http://dx.doi.org/10.1155/2015/187173.

Litjens et al, "A Survey on Deep Learning in Medical Imagine Analysis", Diagnostic Image Analysis Group, Radboud University Medical Center, Nijmegen, The Netherlands, published Feb. 21, 2017, pp. 1-38.

Chenglei Wu et al., "Model-based teeth reconstruction", ACM Transactions on Graphics (TOG), ACM, US, vol. 35, No. 6, Nov. 11, 2016, pp. 1-13.

International Search Report dated Feb. 26, 2019, for corresponding International Patent Application No. PCT/EP2018/086686, filed Dec. 21, 2018.

Written Opinion of the International Searching Authority dated Feb. 26, 2019, for corresponding International Patent Application No. PCT/EP2018/086686, filed Dec. 21, 2018.

Ahn, B, "The Compact 3D Convolutional Neural Network for Medical Images", Jul. 2, 2017, pp. 1-9, http://cs231n.standord.edu/reports/2017/pdfs/23/pdf, retrieved Dec. 18, 2018.

Auro Tripathy, "Five Insights from GoogLeNet You Could Use In Your Own Deep Learning Nets", Sep. 20, 2016, pp. 1-21, https://www.slideshare.net/aurot/googlenet-insights?from_action=save, retrieved Dec. 18, 2018.

Bustos et al., "An Experimental Comparison of Feature-Based 3D Retrieval Methods" 2nd International Symposium on 3D Data Processing, Visualization, and Transmission, 3DPVT 2004, Sep. 6-9, 2004, pp. 215-222.

Chaouch, M. and Verroust-Blondet, A., "Alignment of 3D Models", Graphical Models, Mar. 2009, pp. 63-76, vol. 71, No. 2.

Duda et al., "Pattern Classification: Introduction", 2001, Pattern Classification, New York, John Wiley & Sons, US, pp. 1-13.

Duy et al., "Automatic Detection and Classification of Teeth in CT Data", International Conference on Medical Image Computing and Computer-Assisted Intervention—MICCAI 2012, 2012, pp. 609-616.

Everingham et al.,"The PASCAL Visual Object Classes (VOC) Challenge", International Journal of Computer Vision, Sep. 9, 2009, pp. 303-338, vol. 88, No. 2.

Fetcher et al., "A 3D Fully Convolutional Neural Network and a Random Walker to Segment the Esophagus in CT", Apr. 21, 2017, 23 pages, https://arxiv.org/pdf/1704.06544.pdf, retrieved Dec. 18, 2018.

He et al., "Deep Residual Learning for Image Recognition", 2016 IEEE Conference on Computer Vision and Pattern Recognition (CPR), Jun. 2016, pp. 770-778.

Klinder et al., "Automated Model-Based Vertebra Detection, Identification, and Segmentation in CT Images", Medical Image Analysis, Jun. 2009, pp. 471-482, vol. 13, No. 3.

Miki et al. "Tooth Labeling in Cone-Beam CT Using Deep Convolutional Neural Network for Forensic Identification", SPIE 10134, Medical Imaging 2017: Computer-Aided Diagnosis, Mar. 3, 2017, 6 pages.

Miki et al. "Classification of Teeth in Cone-Beam CT Using Deep Convolutional Neural Network", Computers in Biology and Medicine, Jan. 2017, pp. 24-29, vol. 1, No. 80.

Ryu et al. "Analysis of Skin Movement With Respect to Flexional Bone Motion Using MR Images of a Hand", Journal of Biomechanics, 2006, pp. 844-852, vol. 39, No. 5.

Sekuboyina et al., "A Localisation-Segmentation Approach for Multi-Label Annotation of Lumbar Vertebrae Using Deep Nuts", Cornell University Library, 201 Olin Library Cornell University Ithaca, NY 14853, Mar. 13, 2017, 10 pages.

Szegedy et al., "Going Deeper With Convolutions", 2015 IEEE Conference on Computer Vision and Pattern Recognition (CVPR), Jun. 2015, pp. 1-9.

Chen et al. "Deep RBFNet: Point Cloud Feature Learning Using Radial Basis Functions", Cornell University Library, Dec. 11, 2018, 11 pages.

Chen et al. "Fast Resampling of 3D Point Clouds Via Graphs", IEEE Transactions on Signal Processing, Feb. 1, 2018, pp. 666-681, vol. 66, No. 3.

Fang et al. "3D Deep Shape Descriptor", 2015 IEEE Conference on Computer Vision and Pattern Recognition (CVPR), 2015, pp. 2319-2328.

Ghafoorian et al. "EL-GAN: Embedding Loss Driven Generative Adversarial Networks for Lane Detection", Computer Vision—ECCV 2018 Workshops, Jan. 23, 2019, pp. 256-272, vol. 11129.

Ghazvinian Zanjani et al. "Deep Learning Approach to Semantic Segmentation in 3D Point Cloud Intra-oral Scans of Teeth", Proceedings of the 2nd International Conference on Medical Imaging

(56) References Cited

OTHER PUBLICATIONS with Deep Learning, 2019, 22 pages, retrieved online from https://openreview.net/forum?id=ByxLSoblgV.
Gomes et al. "Efficient 3D Object Recognition Using Foveated Point Clouds", Computers & Graphics, May 1, 2013, pp. 496-508, vol. 37.
Guo et al. "3D Mesh Labeling Via Deep Convolutional Neural Networks", ACM Transactions on Graphics, Dec. 2015, pp. 1-12, vol. 35, No. 1, Article 3.
Hermosilla et al. "Monte Carlo Convolution for Learning on Non-Uniformly Shaped Point Clouds", ACM Transactions on Graphics, Nov. 2018, 12 pages, vol. 37, No. 6, Article 235.
Hou et al. "3D-SIS: 3D Semantic Instance Segmentation of RGB-D Scans", Computer Vision and Pattern Recognition (CPR), Apr. 29, 2019, 14 pages.
Huang et al. "Edge-Aware Point Set Resampling", ACM Transactions on Graphics, 2013, pp. 1-12, vol. 32, No. 1, Article 9.
Ku et al. "Joint 3D Proposal Generation and Object Detection from View Aggregation", IEEE/RSJ International Conference on Intelligent Robots and Systems (IROS), Jul. 12, 2018, pp. 1-8.
Le T. and Duan Y. "PointGrid: A Deep Network for 3D Shape Understanding", Proceedings of the IEEE Conference on Computer Vision and Pattern Recognition, Jun. 18-23, 2018, pp. 9204-9214.
Li et al. "SO-Net: Self-Organizing Network for Point Cloud Analysis", Eye In-Painting with Exemplar Generative Adversarial Networks, Jun. 2018, pp. 9397-9406.
Liu, C. and Furukawa, Y. "MASC: Multi-scale Affinity with Sparse Convolution for 3D Instance Segmentation", Computer Vision and Pattern Recognition (CPR), Feb. 12, 2019, 4 pages.
Qi et al. "Frustum PointNets for 3D Object Detection from RGB-D Data", Computer Vision and Pattern Recognition (CPR), Apr. 13, 2018, 15 pages.
Qi et al. "PointNet++: Deep Hierarchical Feature Learning on Point Sets in a Metric Space", Conference on Neural Information Processing Systems (NIPS), Jun. 2017, 14 pages.
Ravanbakhsh et al. "Deep Learning With Sets and Point Clouds", Feb. 24, 2017, 12 pages, retrieved online from https://arxiv.org/abs/1611.04500.
Silva et al. "Automatic Segmenting Teeth in X-Ray Images: Trends, A Novel Data Set, Benchmarking and Future Perspectives", Feb. 9, 2018, 33 pages, retrieved online from https://arxiv.org/pdf/1802.03086.pdf.
Skrodzki et al. "Directional Density Measure to Intrinsically Estimate and Counteract Non-Uniformity in Point Clouds", Computer Aided Geometric Design, Aug. 2018, pp. 73-89, vol. 64.
Shaoqing et al. "Mask R-CNN", Proceedings of the IEEE International Conference on Computer Vision, 2017, pp. 2961-2969.
Tian, S. "Automatic Classification and Segmentation of Teeth on 3D Dental Model Using Hierarchical Deep Learning Networks" IEEE Journals & Magazine, Jun. 21, 2019, pp. 84817-84828.
Wang et al. "SGPN: Similarity Group Proposal Network for 3D Point Cloud Instance Segmentation", CVF Conference on Computer Vision and Pattern Recognition, Nov. 23, 2017, 13 pages.
Wu et al. "3D ShapeNets: A Deep Representation for Volumetric Shapes", 2015 IEEE Conference on Computer Vision and Pattern Recognition (CVPR), 2015, pp. 1912-1920.
Xu et al. "SpiderCNN: Deep Learning on Point Sets with Parameterized Convolutional Filters", Computer Vision—EECV, 2018, 16 pages.
Yi et al. "GSPN: Generative Shape Proposal Network for 3D Instance Segmentation in Point Cloud", Proceedings of the IEEE/CVF Conference on Computer Vision and Pattern Recognition (CVPR), 2019, 13 pages.
Non-published U.S. Appl. No. 17/415,465, filed Jun. 17, 2021.
Non-published U.S. Appl. No. 17/626,744, filed Jan. 12, 2022.
Gutierrez-Becker et al. "Learning Optimization Updates for Multimodal Registration", Medical Image Computing and Computer-Assisted Intervention—MICCAI 2016, 2016, pp. 19-27.
Hosntalab et al. "A Hybrid Segmentation Framework for Computer-Assisted Dental Procedures", IEICE Transactions on Information and Systems, Oct. 2009, pp. 2137-2151, vol. E92D, No. 10.
Studholme et al. "Automated Three-Dimensional Registration of Magnetic Resonance and Positron Emission Tomography Brain Images by Multiresolution Optimization of Voxel Similarity Measures", Medical Physics, 1997, pp. 25-35, vol. 24. No. 1.

\* cited by examiner

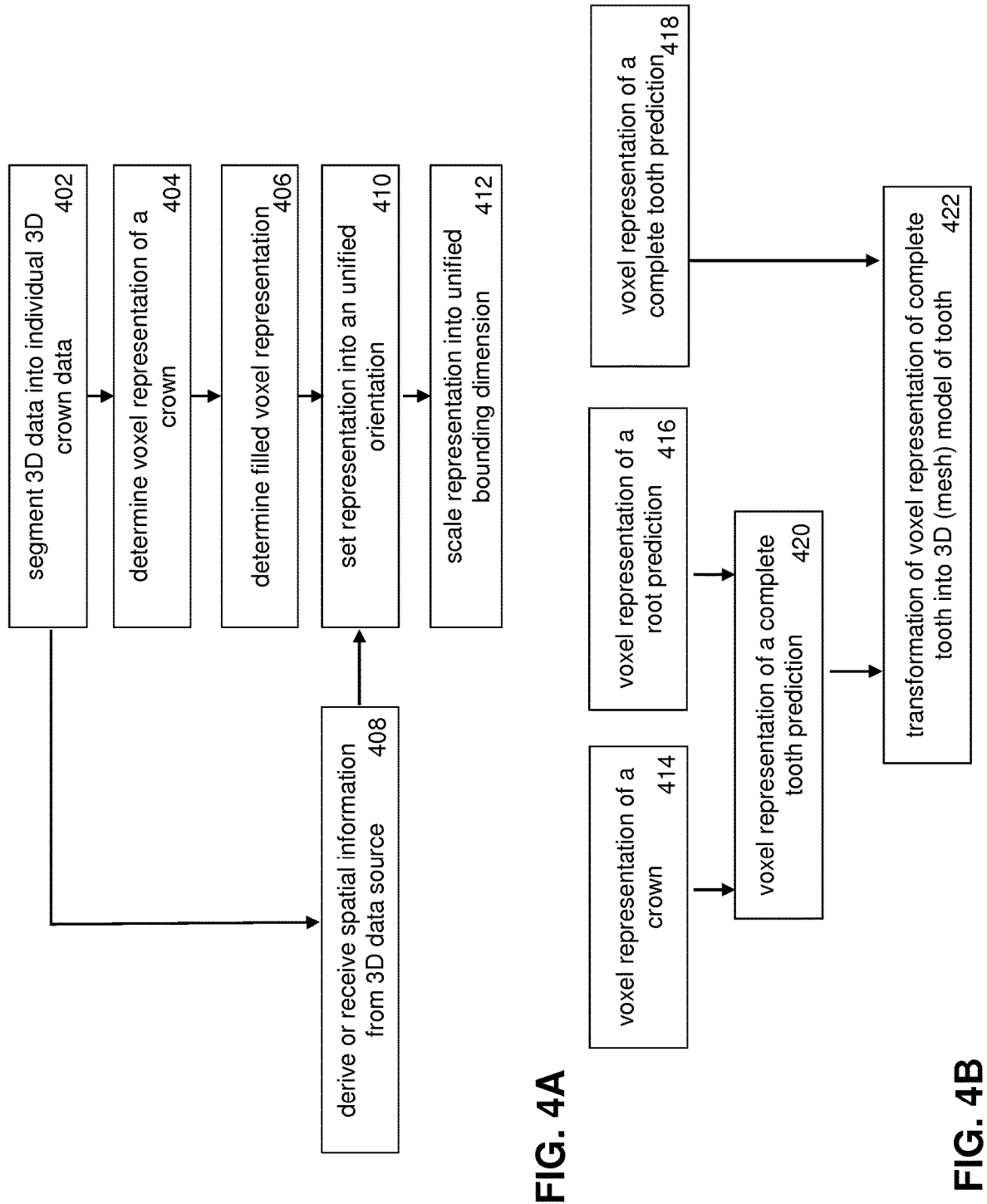

| Class | No. Heldout Samples | Mean Dice Coefficient | Highest Dice Coefficient |
|---|---|---|---|
| Incisors | 35 | 0.79 | 0.88 |
| Canines | 37 | 0.84 | 0.91 |
| Pre-molars | 60 | 0.69 | 0.82 |
| Molars | 35 | 0.74 | 0.85 |
| All | 167 | 0.76 | 0.91 |

FIG. 6A

| Tooth Index | No. Heldout Samples | Mean Dice Coefficient | Highest Dice Coefficient |
|---|---|---|---|
| 11 | 5 | 0.79 | 0.84 |
| 12 | 6 | 0.82 | 0.88 |
| 13 | 4 | 0.81 | 0.87 |
| 14 | 9 | 0.66 | 0.72 |
| 15 | 5 | 0.67 | 0.72 |
| 16 | 5 | 0.74 | 0.78 |
| 17 | 3 | 0.77 | 0.81 |
| 21 | 6 | 0.83 | 0.88 |
| 22 | 4 | 0.81 | 0.84 |
| 23 | 6 | 0.84 | 0.89 |
| 24 | 4 | 0.68 | 0.77 |
| 25 | 6 | 0.70 | 0.81 |
| 26 | 1 | 0.80 | 0.80 |
| 27 | 3 | 0.72 | 0.74 |
| 28 | 2 | 0.74 | 0.79 |
| 31 | 1 | 0.82 | 0.82 |
| 32 | 5 | 0.80 | 0.86 |
| 33 | 10 | 0.83 | 0.91 |
| 34 | 9 | 0.67 | 0.80 |
| 35 | 8 | 0.72 | 0.82 |
| 36 | 6 | 0.73 | 0.79 |
| 37 | 6 | 0.75 | 0.82 |
| 41 | 4 | 0.69 | 0.75 |
| 42 | 4 | 0.78 | 0.84 |
| 43 | 16 | 0.85 | 0.90 |
| 44 | 11 | 0.72 | 0.82 |
| 45 | 9 | 0.71 | 0.79 |
| 46 | 7 | 0.75 | 0.85 |
| 47 | 2 | 0.72 | 0.73 |
| All | 167 | 0.76 | 0.91 |

FIG. 6B

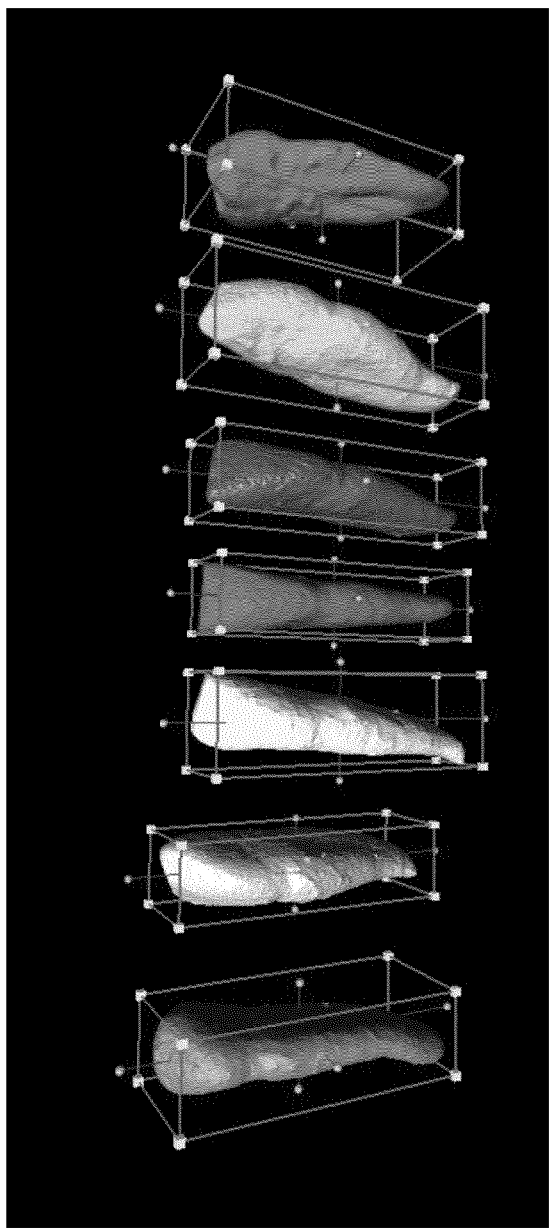
FIG. 9B
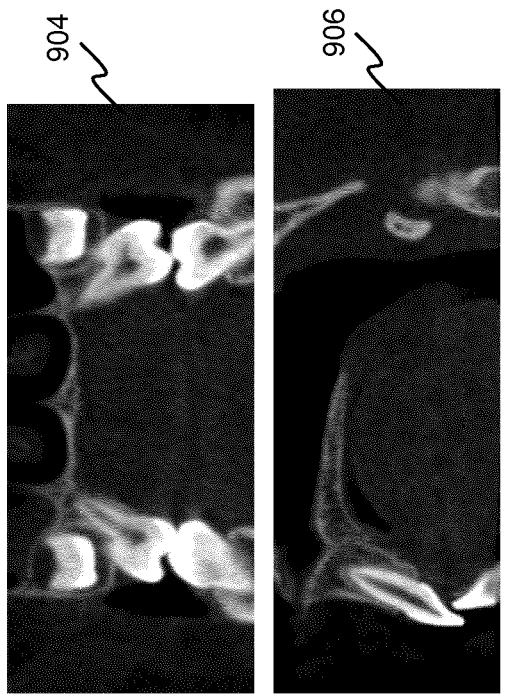
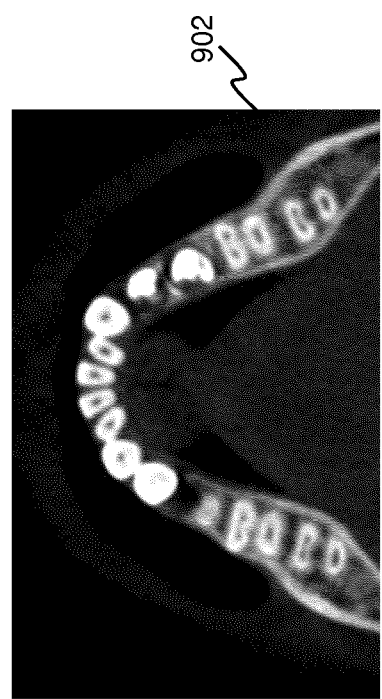
FIG. 9A

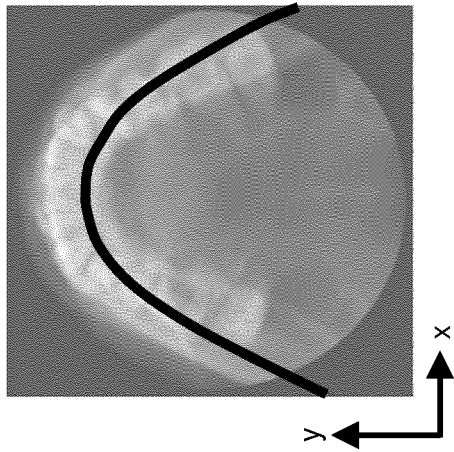
FIG. 12
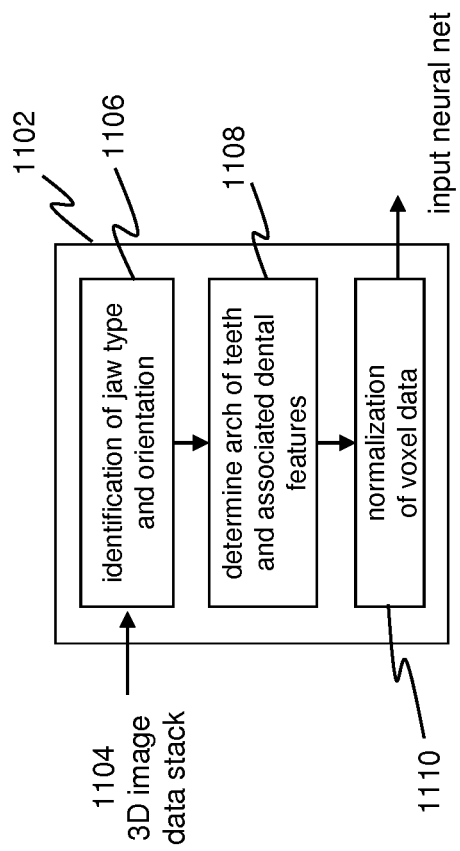
FIG. 11A
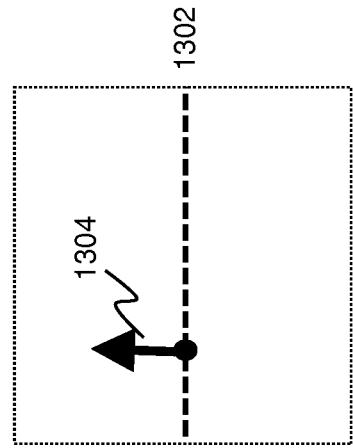
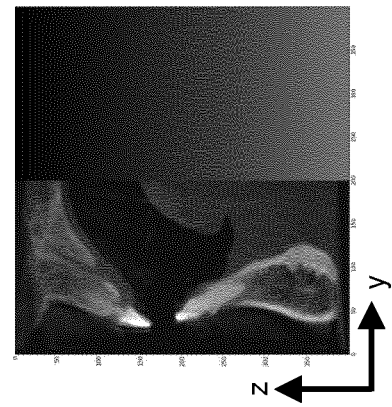
FIG. 13A

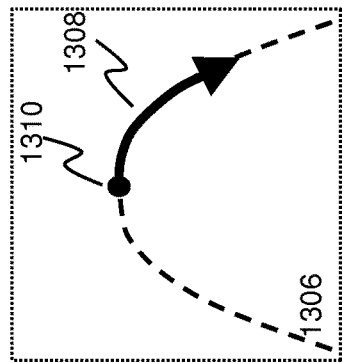
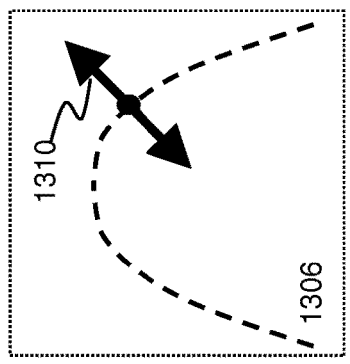
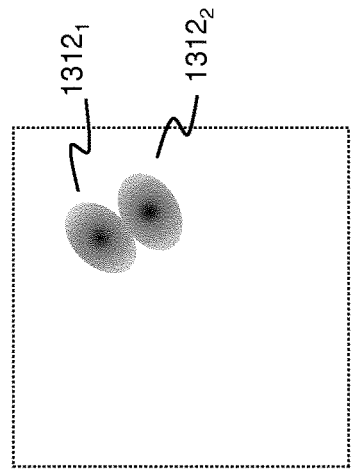
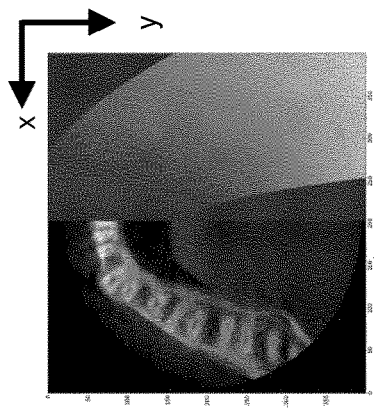
FIG. 13B
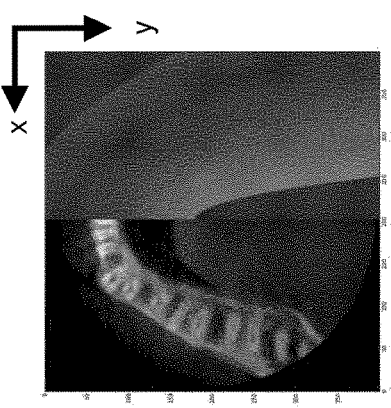
FIG. 13C
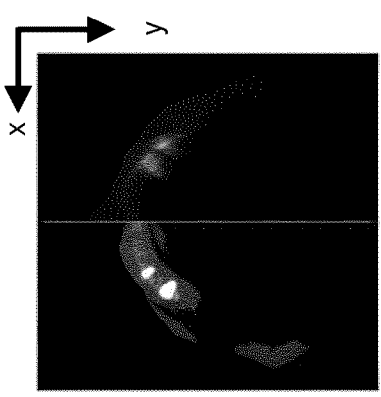
FIG. 13D

AUTOMATED 3D ROOT SHAPE PREDICTION USING DEEP LEARNING METHODS

CROSS-REFERENCE TO RELATED APPLICATION

The present application is a national stage of and claims priority of International patent application Serial No. PCT/EP2018/086686, filed Dec. 21, 2018, and published in English as WO 2019/122373.

FIELD OF THE INVENTION

The invention relates to automated 3D root shape prediction using deep learning methods, and, in particular, though not exclusively, to systems and methods for automated 3D root shape prediction using deep learning, a method for training such deep learning neural network, and a computer program product for using such method.

BACKGROUND OF THE INVENTION

Reliable modelling of teeth plays a very important role in many dental applications including (but not limited to) computer-aided orthodontics and dental treatment simulation systems. For example, in periodontology, diagnosis and treatment is directly related to the anatomy of the roots, in orthodontic treatment planning the configuration of the root, the shape of the root and the bone-root ratio have an enormous impact on the bio-mechanics of the treatment, in exodontics, the field of pulling teeth, the knowledge of the shape of the roots is essential and in endodontics, the root canals and the associated root canal treatment are directly related to the anatomy of the root and the root configuration.

An accurate 3D model of a complete tooth, i.e. a model that includes both the crown and the root, can be obtained using suitable 3D X-ray based CT scanning techniques such as Cone Beam Computed Tomography (CBCT). However, accurate 3D CT data of a patient and software to process such 3D CT data into a representation of a full tooth 3D model is not always available. An X-ray based 3D imaging system is an expensive system which is not always available to a dental specialist. Moreover, in general there is a need to keep exposure of patients to radiation to a minimum. Therefore, systems are developed which are able to determine a 3D representation of a complete tooth on the basis of only the visual part of a tooth, the crown.

For example, U.S. Pat. No. 8,639,477 describes a system for the 3D modeling of a complete tooth in which a mathematical model of a reference tooth (a parametrized 3D surface mesh) is matched based on parameters and morphed on the basis of 3D image data of a patient's crown. Such crown 3D image data can nowadays be easily obtained using an optical intra-oral teeth scanner. In the scheme of U.S. Pat. No. 8,639,477, the shape information of the crown is used to reshape a generic 3D tooth model, including the shape of the root. Similarly, U.S. Pat. No. 8,135,569 describes a system for 3D modelling of a complete tooth by making use of a landmark-based method, morphing a reference tooth on the basis of image data of a patient's crown and optionally X-ray data of the tooth of the patient. The X-ray data allow reducing discrepancies between the shape of the root of the morphed generic 3D tooth model and the actual root shape of the patient's tooth so that an improved 3D approximation of the complete tooth can be determined.

These known 3D modeling techniques are based on crown morphology, which is a particular field in dental technology which examines the relation between a limited number of macroscopic features (dimensions of the crown, shape of the crown, etc.) of a tooth and the shape of its root. Such relations can be used to define a mathematical reference model which is used to approximate the shape of the root on the basis of features of the crown. Although the prior art systems may provide an approximation of a 3D model of a root on the basis of crown information, the accuracy and reliability of such approximation is limited and still may exhibit relatively large deviations when compared with the real anatomical shape of the root. Moreover, the approximation may only be reliable to a certain extent if specific 3D reference models are used for specific classes, both for specific tooth classes (e.g. molar, canine, bicuspid), as well as classes describing the patient (e.g. age, gender). Such approach would require developing a specific mathematical reference model for each specific tooth/patient class.

A further problem of the prior art is that when constructing a complete 3D tooth on the basis of the estimated 3D root model and the 3D crown model, the surfaces in the transition area between the predicted root and the original crown may require additional smoothing and/or other processing which may introduce changes in the shape of the complete 3D tooth which deviate from the actual anatomical shape of the tooth. Additionally, it is noteworthy that in order to be accurate, the above described systems may require additional inputs aside from the crown 3D image data such as the applicable classes (in the tooth and in the patient domain) and x-ray images.

Currently, in the field of imaging, in particular medical imaging, more advanced techniques such as deep learning techniques can be utilized for 3D modeling. These neural networks are trained to learn the features that optimally represent relevant aspects within the data. Such deep learning algorithms include a multilayer, deep neural network that transforms input data to outputs while learning increasingly higher-level features. A successful neural network model for image analysis is the so-called convolutional neural network (CNN). CNNs contain many layers that transform their input using kernels, also known as convolution filters, consisting of a relatively small sized matrix. An overview of the usage of CNNs for medical imaging can be found in the article by Litjens et al., A Survey on Deep Learning in Medical Image Analysis, published 21 Feb. 2017 arXiv (submitted to Computer Vision and Pattern Recognition).

The accuracy and reliability of a trained deep neural network relies heavily on the quality and quantity of the data that are used to train the neural network. Cone Beam Computed Tomography (CBCT) is the most used 3D imaging technique in dental applications and an extensive amount of CBCT data sets containing 3D dento-maxillofacial structures are in principle available for training a neural network. Image analysis of CBCT image data and the generation of a large amount of high-quality training data on the basis of these CBCT image data however poses a substantial problem. In CBCT scans the radio density, measured in Hounsfield Units (HUs), is not consistent because different areas in the scan appear with different greyscale values depending on their relative positions in the organ being scanned. HUs measured from the same anatomical area with both CBCT and medical-grade CT scanners are not identical and are thus unreliable for determination of site-specific, radiographically-identified measured density.

Moreover, again considering the problem of the availability of accurate and sufficient training data, CBCT systems for scanning dento-maxillofacial structures do not employ a standardized system for scaling the grey levels that represent the reconstructed density values. These values are as such arbitrary and in the absence of such a standardization, it is difficult to interpret the grey levels or even impossible to compare the values resulting from different machines. Moreover, the teeth roots and jaw bone structure(s) have similar densities making it is difficult for a computer to distinguish between voxels belonging to teeth and voxels belonging to a jaw. Additionally, CBCT systems are very sensitive to so-called beam hardening, which produces dark streaks between two high attenuation objects (such as metal or bone), with surrounding bright streaks.

The above-mentioned problems make the realization of a (sufficiently trained) deep learning system that is capable of automated 3D root shape prediction on the basis of 3D crown information very challenging. Hence, there is a need in the art for computer systems that are capable of automatically generating an anatomically accurate prediction of 3D root shapes on the basis of image data of 3D crown shapes.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including a functional or an object oriented programming language such as Java™, Scala, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer, server or virtualized server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), or graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In a first aspect, the invention relates to a computer-implemented method for automated 3D root shape prediction. In an embodiment, the method may comprise: a pre-processor receiving 3D data defining at least one 3D representation of a tooth and processing the 3D data, the processing including: transforming at least part of the 3D data into a voxel representation of a crown, the voxel representation defining a voxel space that fits the input space of a first 3D deep neural network executed on a computer; the pre-processor providing the voxel representation of the crown to the input of the 3D deep neural network, the 3D deep neural network being trained on the basis of clinical 3D data defining 3D representations of real teeth; the first 3D deep neural network generating a voxel representation of a predicted root or a complete tooth comprising the predicted root on the basis of the voxel representation of the crown, wherein the generation of the voxel representation of the predicted root or the complete tooth includes: determining voxel activations for voxels in a voxel space of the output of the 3D deep learning network, each voxel activation representing a probability measure defining the probability that a voxel is part of the root or the complete tooth; and, determining whether a voxel activation is part of the root or the complete tooth by comparing the voxel activation with a voxel activation threshold value.

In another embodiment, the method may comprise a pre-processor (104) receiving 3D data (102) defined in a voxel space, the voxel space defining a 3D volume, the voxel space comprising a voxel representation of a crown, and processing the voxel representation such that it is in a scale, position and orientation that corresponds to voxel representations that are used to train a first 3D deep neural network (106,210); the pre-processor (104) providing the voxel representation of the crown to the input of the first 3D deep neural network (106), the first 3D deep neural network being trained on the basis of a training set of pre-processed clinical 3D data (202) defining 3D representations of real teeth, the trained deep neural network (106,210) being configured to predict an anatomically accurate voxel representation (212) of a root corresponding to the crown or a voxel representation (214) of a complete tooth; the first 3D deep neural network (106,210) generating a voxel representation of a predicted root (212) or of a complete tooth (214) comprising the predicted root on the basis of the voxel representation of the crown, wherein the generation of the voxel representation of the predicted root or the complete tooth includes: determining voxel activations for voxels in a voxel space of the output of the first 3D deep learning network, each voxel activation representing a probability measure defining the probability that a voxel is at least part of the root or of the complete tooth; and, determining whether a voxel activation is part of the root or of the complete tooth by comparing the voxel activation with a voxel activation threshold value. In an embodiment, the threshold value may represent a probability of more than 0.5.

Hence, the 3D deep neural network is trained to automatically learn the anatomical features available from the received voxel representation of the crown to (at least) generate an anatomically accurate prediction of a root representation, wherein the resulting root model will closely fit the crown model in order to form a full tooth model. Due to the fact that such features can be learned from any potential training sample (a sample being the voxel representation of the crown), and that the 3D deep neural network will determine which features are relevant, the method has the ability to more accurately make use of any relevant information in said voxel representation. In other words, where prior art may be limited to a specific set of input parameters, the method proposed has the potential to make use of more input information and will determine which features are relevant during training.

Additionally, the 3D deep neural network will learn a generalization of 3D image data representing root sections based on crown sections. This generalization is however more flexible (considering the potential different shapes that can be generated for either predicted root or complete tooth) than making use of a template root as is done in prior art. It is also worthy to note that the method does not require separate input that indicates tooth classes (canine, molar, etc.) and/or patient classes (age, gender, etc.). In effect, the 3D deep neural network has the potential to recognize relevant features that are the result of such a classification directly from the received voxel representation. This is however (at least) dependant on the amount of available training samples varied across such classes, and memory bandwidth available within the feature representations in the 3D deep neural network.

In an embodiment, the method may include a post-processor receiving the voxel representation of the predicted root generated by the first 3D deep neural network and processing the voxel representation of the predicted root and the 3D crown, wherein the processing may include: merging the voxels of the 3D root and the 3D crown model into a voxel representation of a complete 3D tooth. In yet another embodiment, the post-processor may transform the voxel representation of the complete 3D tooth in a 3D mesh of a complete tooth.

Hence, the invention allows automatic generation of at least an anatomically accurate prediction of a 3D root shape by a trained deep neural network executed on a computer. The deep neural network may generate the 3D root shape on the basis of 3D crown data set, e.g. a 3D surface mesh generated by an intra-oral optical scanner or a 3D data generated by an X-ray scanner e.g. a CBCT scanner. As the neural network is trained on the basis of clinical data of 3D models of whole teeth, the network will generate an anatomical accurate prediction of a 3D root model, wherein the 3D root model accurately fits the 3D crown data that were fed to the input of the neural network. This way, the computer may construct an accurate 3D model of the whole tooth on the basis of the generated 3D root representation and the 3D crown model. Accurate 3D tooth models are of considerable value in numerous dental applications including but not limited to periodontology diagnosis and treatment, orthodontic treatment planning, exodontics and endodontics.

In a further embodiment, the two previous described voxel spaces (one for the voxel representation of the crown and one for the voxel representation of the root) are considered as one space, effectively the 3D space that can potentially contain the entire individual tooth. Voxels that are part of the received 3D crown are appropriately represented in the complete tooth space. This complete tooth space, including voxel representation of the 3D crown, is provided to the input of a 3D deep neural network. The trained 3D deep neural network may then generate a voxel representation of the complete tooth in a 3D space having the same dimensions of the input space.

In an embodiment, the method may further comprise: a post-processor receiving the voxel representation of the predicted root generated by the first 3D deep neural network and processing the voxel representation of the predicted root and the 3D crown, the processing including: merging the voxels of the 3D root and the 3D crown model into a voxel representation of a complete 3D tooth; and, optionally, transforming the voxel representation of the complete 3D tooth in a 3D mesh of a complete tooth.

In an embodiment, the 3D data may define a 3D representation of at least part of a dentition, the processing by the pre-processor further including: segmenting the 3D data into at least one 3D data set, the 3D data set representing a 3D crown of a tooth of the dentition; and, transforming the 3D data set into a voxel representation of the crown, the voxel representation matching the voxel space of the input of the first 3D deep neural network.

In an embodiment, the 3D data received by the pre-processor may be 3D data generated by an optical scanner, preferably an intra-oral optical scanner, the 3D data defining a 3D surface mesh representing of at least part of a dentition comprising a plurality of crowns.

In an embodiment, the processing by the pre-processor may further include: segmenting the 3D mesh into a plurality of segmented 3D meshes wherein each segmented 3D mesh represents a 3D crown of the dentition; transforming each segmented 3D surface mesh into a voxel representation of the crown, the voxel representation matching the voxel space of the input of the first 3D deep neural network.

In an embodiment, the 3D data received by the pre-processor may be generated by an X-ray scanner, preferably a CBCT scanner, the 3D data defining a voxel representation of at least part of a dento-maxillofacial structure, a voxel being associated with a radiation intensity value or density value, the dento-maxillofacial structure including a plurality of tooth of at least part of a dentition.

In an embodiment, the processing by the pre-processor may further include: classifying at least part of the voxels representing the dento-maxillofacial structure into at least one of jaw, teeth and/or nerve voxels; segmenting the classified teeth voxels into one or more 3D data sets, each of the one or more 3D data sets defining a voxel representation of a tooth in the dentition of the dento-maxillofacial structure.

In an embodiment, the voxels representing the dento-maxillofacial structure are classified using a second 3D deep neural network.

In an embodiment, the processing by the pre-processor may further include: classifying at least part of the voxels representing the dento-maxillofacial structure into at least one of jaw, teeth and/or nerve voxels using a second 3D deep neural network; the second 3D deep neural network being trained on the basis of 3D image data of dento-maxillofacial structures, optionally one or more 3D positional features derived from the 3D image data of the training set, and one or more 3D models of parts of the dento-maxillofacial structures of the 3D image data of the training set, the one or more 3D models being used as target during training of the first deep neural network; and, segmenting the classified voxels into one or more 3D data sets, each of the one or more 3D data sets defining a voxel representation of a tooth in the dentition of the dento-maxillofacial structure.

In an embodiment, the processing by the pre-processor may further include: providing a further voxel representation of the dento-maxillofacial structure to the input of a third 3D deep neural network, the third deep neural network being trained to determine for each voxel of the voxel representation at the input at least one 3D positional feature, a 3D positional feature including a measure indicating a likelihood that a voxel represents jaw, teeth and/or nerve tissue, wherein the further voxel representation of the dento-maxillofacial structure is a low-resolution version of the voxel representation of the dento-maxillofacial structure.

In an embodiment, the resolution of the further voxel representation may be at least three times lower than the resolution of the first voxel presentation.

In an embodiment, the third 3D deep neural network may be trained based on the 3D image data of dento-maxillofacial structures and the one or more 3D models of parts of the dento-maxillofacial structures of the 3D image data of the training set for training the second deep neural network.

In an embodiment, the processing by the pre-processor may further include: providing the one or more 3D positional features and the voxel representation of the dento-maxillofacial structure to the second 3D deep neural network and the second 3D deep neural network using the one or more positional features to classify at least part of the voxels in the voxel space into at least one of jaw, teeth and/or nerve voxels.

In an embodiment, the second deep neural network may comprise a plurality of first 3D convolutional layers, the output of the plurality of first 3D convolutional layers being connected to at least one fully connected layer, wherein the plurality of first 3D convolutional layers are configured to process a first block of voxels from the first voxel representation and wherein the at least one fully connected layer is configured to classify voxels of the first block of voxels into at least one of jaw, teeth and/or nerve voxels In an embodiment, the second deep neural network may further comprise a plurality of second 3D convolutional layers, the output of the plurality of second 3D convolutional layers being connected to the at least one fully connected layer, wherein the plurality of second 3D convolutional layers are configured to process a second block of voxel from the first voxel representation, the first and second block of voxels having the same or substantially the same centre point in the image volume and the second block of voxels representing a volume in read-world dimensions that is larger than the volume in real-world dimensions of the first block of voxels, the plurality of second 3D convolutional layers being configured to determine contextual information associated with voxels of the first block of voxels that is provided to the input of the plurality of first 3D convolutional layers.

In an embodiment, the processing by the pre-processor may further include: determining one or more 3D positional features on the basis of the voxels representing the dento-maxillofacial structure, a 3D positional feature defining position information of voxels in the voxel space of the voxels of at least part of a dento-maxillofacial structure; providing the one or more 3D positional features to the second 3D deep neural network and the second 3D deep neural network using the one or more positional features to classify at least part of the voxels in the voxel space into at least one of jaw, teeth and/or nerve voxels.

In an embodiment, the position information may define a distance, preferably a perpendicular distance, between voxels in the voxel space and a first dental reference plane in the voxel space; a distance between voxels in the voxel space and a first dental reference object in the voxel space; and/or, positions of accumulated intensity values in a second dental reference plane of the voxels space, wherein an accumulated intensity value at a point in the second dental reference plane includes accumulated intensity values of voxels on or in the proximity of the normal running through the point in the second dental reference plane.

In an embodiment, the second deep neural network may comprise a first data processing path including at least a first plurality of 3D convolutional layers, preferably a first set of 3D CNN feature layers, and a second data processing path including a second plurality of 3D convolutional layers, preferably a second set of 3D CNN feature layers, parallel to the first path, for receiving the one or more 3D positional features, the second plurality of 3D convolutional layers being configured to encode relevant information from positional information associated with blocks of voxels that are fed to the input of the first plurality of 3D convolutional layers.

In an embodiment, the first 3D deep neural network may include a plurality of 3D convolutional layers connected via one or more densely connected layers to a plurality of 3D deconvolutional layers and wherein the first deep neural network is trained on the basis of voxel representations of crowns and associated roots or on the basis of voxel representations of crowns and associated teeth which, preferably at least part of the voxel representations being derived from segmented 3D X-ray data, preferably 3D CBCT data, representing one or more dento-maxillofacial structures.

In a further aspect, the invention may relate to an computer-implemented method for training a 3D deep learning neural network to generate a prediction of 3D root shape comprising: a computer receiving training data, the training data including clinical 3D data comprising voxel representations of crowns and associated roots or on the basis of voxel representations of crowns and associated teeth wherein at least part of the voxel representations being derived from segmented 3D X-ray data, preferably 3D cone beam CT (CBCT) data; offering a voxel presentation of a crown to the input of the 3D deep neural network and the 3D deep neural network generating a voxel representation of a predicted root; optimizing values of one or more network parameters of the 3D deep neural network by minimizing a loss function representing a deviation between the voxel representation of a predicted root and the voxel representation of root that is associated with the voxel representation of the crown that was offered to the input of the 3D deep neural network.

In an embodiment, the method may include storing the optimized values in a computer readable storage medium, the optimized values defining one or more network parameters of a trained neural network configured to, when provided with a voxel representation of a crown, predict an anatomically accurate voxel representation of a root corresponding to the crown or a voxel representation of a complete tooth.

In an embodiment, the 3D deep neural network may include a plurality of 3D convolutional layers connected via one or more densely connected layers to a plurality of 3D deconvolutional layers.

In a further aspect, the invention may relate to a computer system, preferably a server system, adapted to automatically predict a 3D root shape comprising: a computer readable storage medium having computer readable program code embodied therewith, the program code including a pre-processing algorithm and at least a trained first 3D deep neural network, the computer readable program code; and a processor, preferably a microprocessor, coupled to the computer readable storage medium, wherein responsive to executing the first computer readable program code, the processor is configured to perform executable operations comprising: the pre-processor receiving 3D data defining at least one 3D representation of a tooth and processing the 3D data, the processing including: transforming at least part of the 3D data into a voxel representation of a crown, the voxel representation defining a voxel space that fits the input space of a 3D deep neural network executed on a computer; the pre-processor providing the voxel representation of the crown to the input of the 3D deep neural network, the 3D deep neural network being trained on the basis of clinical 3D data defining a 3D representation of real teeth; the 3D deep neural network generating a voxel representation of a predicted root or a complete tooth comprising a predicted root on the basis of the voxel representation of the crown, wherein the generation of the voxel representation of a predicted root or a complete tooth comprising a predicted root includes: determining voxel activations for voxels in a voxel space of the output of the 3D deep learning network, each voxel activation representing a probability measure defining the probability that a voxel is part of the root or the complete tooth; and, determining whether a voxel activation is part of the root or the complete tooth by comparing the voxel activation with a voxel activation threshold value.

In a further aspect, the invention may relate to a computer system, preferably a server system, adapted to automatically predict a 3D root shape comprising a computer readable storage medium having computer readable program code embodied therewith, the program code including a pre-processing algorithm and at least a trained 3D deep neural network; and a processor, preferably a microprocessor, coupled to the computer readable storage medium, wherein responsive to executing the computer readable program code, the processor is configured to perform executable operations as defined in any of the method steps described above.

The invention may also relate of a computer program product comprising software code portions configured for, when run in the memory of a computer, executing any of the methods as described above.

Throughout this text, where reference is made to '3D image data' or '3D data, this is intended to mean any format of 3D image data, e.g. (a) 3D surface mesh(es), 3D point cloud(s), data in a 3D (voxel) space representing either a volume, surface, or density values on a specific 3D coordinate, etc. Where reference is made to '3D model', this is intended to refer to (a) 3D surface mesh(es) unless it is stated otherwise. Further, a complete tooth is considered to consist of the combination of the 'crown' and the 'root' part, with 'root' being defined as any part of the 3D volume occupied by the complete tooth that is not 'crown'.

The invention will be further illustrated with reference to the attached drawings, which schematically will show embodiments according to the invention. It will be understood that the invention is not in any way restricted to these specific embodiments.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 4A and FIG. 4B depict schematics illustrating pre-processing and post-processing of 3D data according to various embodiments of the invention;

FIGS. 6A and 6B show tables of Dice coefficients as determined from an exemplary embodiment of the system;

FIGS. 9A and 9B depict examples of 3D CT image data and 3D optical scanning data respectively;

FIGS. 11A and 11B illustrate a flow diagram and a neural network for determining dento-maxillofacial features according to an embodiment of the invention;

FIG. 12 provides a visualization containing the summed voxel values from a 3D image stack and a curve fitted to voxels representing a dento-maxillofacial arch;

FIG. 13A-13E depict examples of dento-maxillofacial features according to various embodiments of the invention;

DETAILED DESCRIPTION

Figure 1:
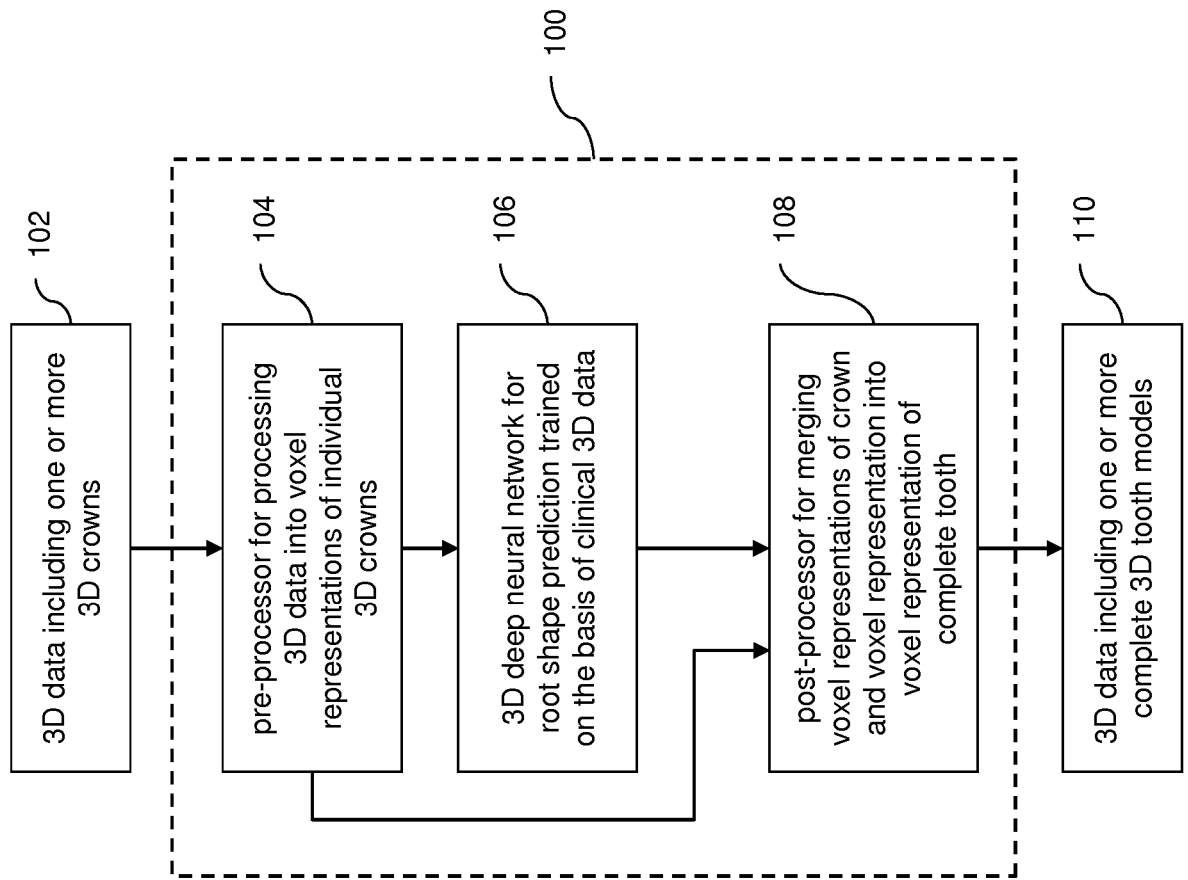
FIG. 1 depicts a high-level schematic of a computer system configured for automatic 3D root shape prediction according to an embodiment of the invention.

In this disclosure embodiments are described of computer systems and computer-implemented methods that use 3D deep neural networks for predicting an anatomically accurate 3D representation of a root on the basis of 3D data defining a 3D representation of a crown (in short 3D crown data). The 3D crown data may be derived from different data sources. For example, the 3D crown data may be derived from a 3D surface mesh representing teeth crowns of dentition generated by an 3D optical scanner, e.g. an intra-oral optical scanner. Alternatively, the 3D crown data may be derived from e.g. a 3D voxel representation representing a dento-maxillofacial structure (including teeth crowns) generated by a 3D X-ray scanner such as a CBCT scanner. The 3D deep neural network may be trained on the basis of clinical 3D data, e.g. 3D data defining a representation of real teeth. A computer system according to the invention may comprise at least one 3D deep neural network which is trained to generate a voxel representation of an anatomically accurate prediction of a voxel representation of a root on the basis of a voxel representation of a crown. The computer system may be configured to execute a training process which iteratively trains the 3D deep neural network on the basis of training data which are based on clinical 3D data, i.e. 3D representations of real teeth. The training data may be based on 3D CBCT data of segmented dento-maxillofacial structures, in particular individually segmented voxel representations of tooth. The voxel representation of tooth may be divided in two 3D data sets, a voxel representation of a 3D crown and a voxel representation of a 3D root.

Using the thus generated training set will result in a trained deep neural network that can accurately predict an anatomically accurate voxel representation of a root or a voxel representation of a complete tooth. Hence, the deep learning network is trained to process voxels in a predetermined voxel space, i.e. a volume defining voxels wherein each voxel is associated with a 3D position in the volume. As the computer system is capable of receiving 3D data of different structures and formats, e.g. 3D data generated by CBCT scanner of an intra-oral optical scanner. The computer system comprises a pre-processor that processes the 3D data before being presented to the input of the 3D deep neural network. The pre-processor may transform the 3D data into voxel representations of individual 3D crows, wherein a voxel representation matches the voxel space of the input of the deep neural network. The pre-processing may further include scaling, positioning and/or orienting a voxel representation in a uniform way (both between 3D data in a training set, being intra-set uniformity, and within different training sets, being inter-set uniformity).

Once the deep neural network is trained, it may receive a voxel representation of a crown and predict either a voxel representation of the corresponding root shape or a voxel representation of the complete tooth, including the predicted root shape. Before being presented to the trained deep neural network, 3D input data is pre-processed in a way similar to the pre-processing of the training data so that the 3D crown is set in a scale, position and orientation that corresponds to the one used during the training of the deep neural network. In case the deep neural network is trained to generate a voxel representation of a prediction of a root, a post-processor may merge the voxel representations of the root and the crown (as offered to the input of the deep neural network) into a voxel representation of a complete tooth. Depending on the application, the post-processor may also transform the voxel representation into a 3D model or mesh representation of the tooth. Because the network is trained using clinical 3D data, in particular clinical 3D CBCT data, the predicted root shape will be based on features that are derived by the deep neural network during training.

The computer system, the deep neural network, the pre- and post-processor, the training of the neural network and the method executed by the network and the pre- and post-processors are described hereunder in more detail.

FIG. 1 depicts a high-level schematic of a computer system according to an embodiment of the invention. In particular, FIG. 1 depicts a computer system that is configured to automatically generate 3D data defining a representation of a complete 3D tooth on the basis of 3D input data representing e.g. a crown, a complete tooth, a dento-maxillofacial structure comprising teeth or a dentition. The computer system 100 may comprise a pre-processor, a trained deep neural network and a post-processer. The pre-processor may pre-process the 3D input data 102.

For example, in an embodiment, the pre-processor 104 may derive individual 3D representations of crowns of a dentition from 3D data representing a real-world dento-maxillofacial structure. Such 3D data may be generated using known techniques such as an X-ray or CBCT scanner. Typically, such 3D data includes a volume of voxels (a voxel space) wherein each voxel value represents a radiation intensity value. As the data represents a full dento-maxillofacial structure, the 3D data also includes spatial information about the position of the teeth (and crowns) in the dento-maxillofacial structure. In such case, the pre-processor may execute a segmentation process for segmenting the 3D data of the dento-maxillofacial structure into individually segmented dental structures (e.g. bone, tooth and nerve), including individual representations of complete tooth, typically a voxel representation of a complete tooth. Automated segmentation of 3D CBCT data representing a dento-maxillofacial structure is a non-trivial process due the nature of the CBCT data. For example, in CBCT scans, the radio density, measured in Hounsfield Units (HUs), is not consistent because different areas in the scan appear with different greyscale values depending on their relative positions in the organ being scanned. A further problem is that CBCT systems do not employ a standardized system for scaling the grey levels that represent the reconstructed density values.

In order to enable automated segmentation without any human intervention and/or help, the pre-processor may use a separately trained deep neural network to automatically classify the 3D data into different 3D data sets, wherein a 3D data set defines a voxel representation of a tooth. The segmentation process, the deep neural network for executing such segmentation process and the pre- and post-processing of the 3D data in order to achieve such accurate segmentation will be described hereunder in greater detail with reference to FIG. 8 and further.

The results from the above-described deep neural network for automatic segmentation of teeth from CBCT data may be utilized to generate clinical 3D tooth representations for training of the deep neural network for root shape prediction 106 during a training phase (described in more details hereunder). The segmentation may also be used during the inference phase, wherein 3D CBCT data may be segmented in order to determine a voxel representation of a crown that can be offered to the input of the trained neural network.

In another embodiment, the pre-processor 104 may derive individual 3D models of crowns of a dentition from 3D data generated by an intra-oral optical scanner. Typically, such 3D data set may define a 3D polygon mesh within a predefined 3D space wherein the data forms a collection of vertices, edges and faces that defines the shape of the scanned crowns and part of the gum in the 3D space. As the data represents parts of a 3D dentition structure, the 3D data also includes spatial information about the position of the crowns in the dentition. In order to automatically divide the 3D mesh of the scanned dentition into 3D meshes of individual 3D crown models, the pre-processor may execute a segmentation process in which the 3D surface mesh representing a plurality of crows of a dentition (or a part hereof) is segmented in a plurality of 3D surface meshes wherein each 3D surface mesh represents an individual 3D crown model. This segmentation process may be performed using known methods as described in 'Automatic Tooth Segmentation of Dental Mesh Based on Harmonic Fields' by Liao, 2015.

After the segmentation process, each 3D data set defining a 3D representation of a crown may be converted into a data format that matches the desired input format of the trained 3D deep neural network 106. To that end, the pre-processor may transform the 3D data set defining a 3D representation of a crown into a voxel representation of the crown using a voxel space that fits the 3D input space of the trained 3D deep neural network. Further, the pre-processor may process the 3D data sets such that the orientation of each of the crown models is scaled, positioned and oriented in the voxel space in a uniform way. This pre-processing may include scaling, rotating, mirroring and/or translating the voxels so that the voxel representation of the crown is positioned centred within the voxel space in a predetermined orientation, e.g. such that the tooth (and crown) 'up-down' direction (or axis in a co-ordinate system), as may be derived from its would-be orientation in a patient standing up, may be used to ensure this direction will be consistent across all voxel representations of a crown that are presented as input to deep neural net 106. The pre-processer may mirror the voxel-representation along a plane that is normal to the previously mentioned 'up-down' axis, to ensure that in the space of the voxel representation, the direction of 'crown-to-root' of the clinical tooth is always pointed in the same direction.

A pre-processed voxel representation of a crown is then offered to the input of a 3D deep neural network 108 that is trained to generate a voxel representation of a prediction of root. The 3D deep neural network may be trained produce a voxel representation of a root that that can be combined with the voxel representation of the crown that was offered to the input of the 3D deep neural network. In another embodiment, the 3D deep neural network may be trained to generate a voxel representation that includes crown voxels that were offered to the input of the 3D deep neural network and voxel predictions of a root. As the deep neural network predicts the root shape per individual 3D crown model, the post-processor 108 may be adapted to merge the predicted root shape with the 3D crown data that was used for the input (e.g. a segmented crown shape from the original source, or with the crown shape in the voxel representation as presented to the deep neural network). The post-processer 108 may convert a merged voxel representation of a complete tooth to a 3D model (surface mesh) and may make use of well-known surface mesh operations such as smoothing and decimation. Additionally, in some embodiments, the created 3D models of the complete teeth may be placed back into the original source, maintaining their relative positions to each other, based on the source 3D input. This may be done where a source contains multiple 3D crown representations, as might be the case where the input data are e.g. CBCT scans or intra-oral scans. Post-processor 108 may in that case create a 3D data set 110 in which each presented crown is provided with a predicted root.

Figure 2:
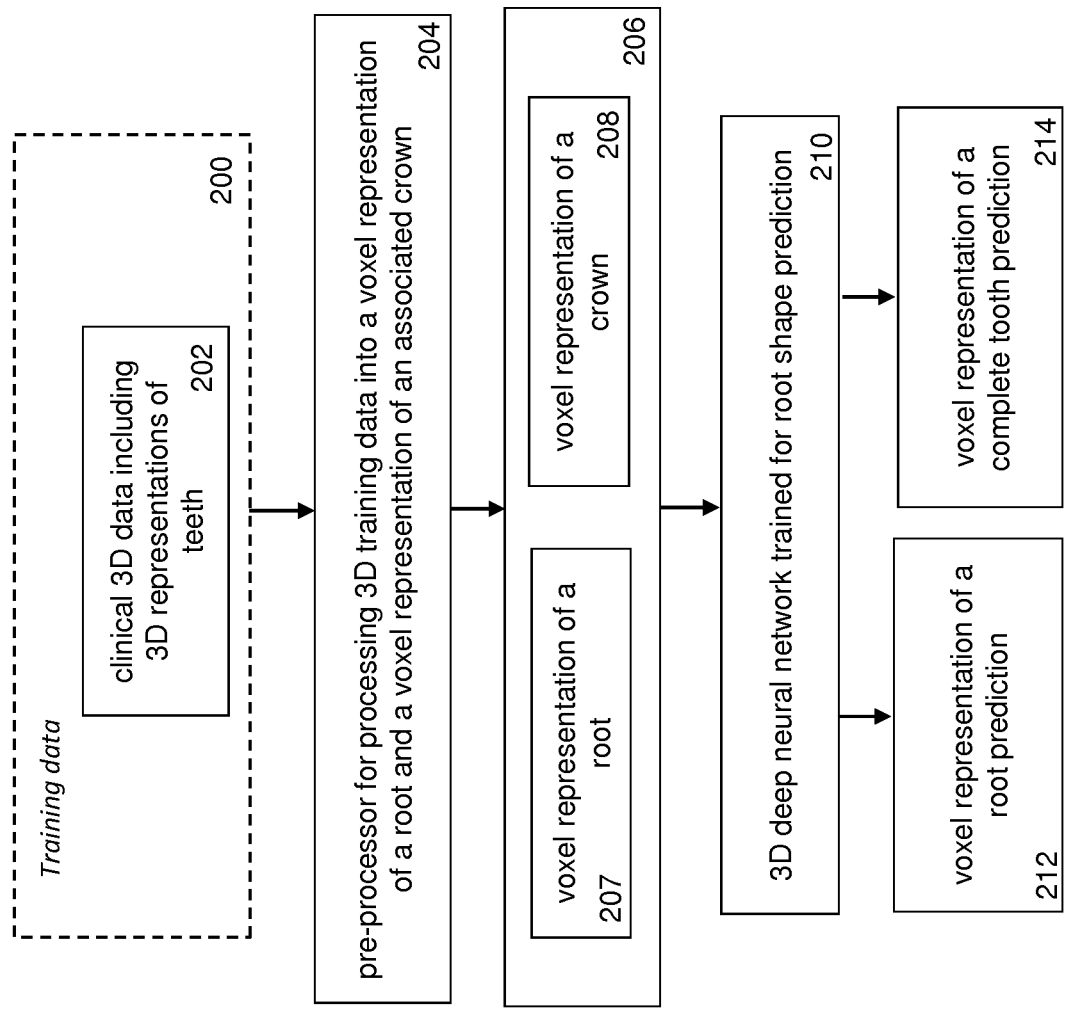
FIG. 2 depicts a flow diagram for training a deep neural network for predicting individual 3D root shapes according to an embodiment of the invention.

FIG. 2 depicts a flow diagram for training a deep neural network for predicting individual 3D tooth root shapes according to an embodiment of the invention. In order to realize the trained 3D deep neural network, a large amount of accurate clinical training data is required. In order to train the 3D deep neural network to accurately predict individual 3D teeth on the basis of 3D crown models, various sources of training data may be used.

The training data 200 may be based on clinical 3D data 202, i.e. 3D data of real teeth of patients, which may be derived from various sources, in particular 3D data generated by X-ray scanners such as CBCT scanners and/or 3D data generated by 3D optical scanners. The 3D data generated by X-ray scanners typically include a voxel representation of at least part of a dento-maxillofacial structure including a plurality of 3D tooth models of at least part of a dentition, wherein each voxel is associated with a radiation intensity value or density value. Similarly, the 3D data of optical scanners typically includes a 3D mesh representing a complete tooth.

As the deep neural network may be trained based on voxel representations of individual tooth models, processing of the clinical 3D data by the pre-processor is required. In an embodiment, the processing by the pre-processor 204 may include determining a plurality of 3D data sets based on clinical 3D CBCT data, wherein each 3D data set may define a 3D representation of a tooth of the dentition in the clinical 3D CBCT data. This way, each 3D data set defines a clinical 3D representation of a tooth. The determination of the 3D data sets requires an accurate automated segmentation process. However, as described with reference to FIG. 1, accurate automated segmentation of 3D CBCT data is not a trivial process and may be realized using a separately trained deep neural network. The segmentation process, the deep neural network for executing such segmentation process and the pre- and post-processing of the 3D data in order to achieve such accurate segmentation will be described hereunder in greater detail with reference to FIG. 8 and further.

Hence, the pre-processor may process the clinical 3D data, typically CBCT data representing a dento-maxillofacial structure, to generate training data for the deep learning network. The pre-processing may include extracting clinical 3D data sets, each clinical 3D data set defining a voxel representation of a tooth 206. Further, the pre-processing may include generating a voxel representation of the crown 208 and an associated voxel representation of the root 207 on the basis of each 3D data set. Further, the pre-processing may include normalizing the orientation, position and/or dimensions of the samples, e.g. crown, root and full tooth, represented by the various voxel representations that are used to train the deep neural network. The re-orientation, re-positioning and scaling of the samples results in normalized samples for training. The normalization enables the deep neural network to accurately train relevant features needed for root prediction.

In an embodiment, the 3D deep learning network 210 may be trained using the voxel representation of the crown as input and the voxel representation of the root as a target label. In another embodiment, the 3D deep learning network may be trained using the voxel representation of the crown as input and the voxel representation of the complete tooth (that includes the root) as a target label.

During training phase, the intermediate outputs of the deep neural network representing a voxel representation of a predicted root 212 or a voxel representation of a predicted tooth 214, may be iteratively evaluated with respect to a target label. This way, after training, during the inference phase, the trained 3D deep learning network is capable of either accurately predicting a 3D root shape or a complete 3D tooth when a voxel representation of an arbitrarily selected 3D crown is offered to the input of the 3D deep neural network.

As described above, voxels of a root 207 and the voxels of a crown 208 may be extracted from a volume of voxels representing a complete tooth 206 (a volume of tooth voxels). Different methods may be used to split the volume tooth voxels into a volume of crown voxels and a volume of root voxels. For example, the volume of tooth voxels may be split on based on a transverse plane, i.e. a plane normal to the 'real-world' 'up-down' axis of the patient, i.e. the longitudinal axis which may be defined as the intersection line of the sagittal plane and the coronal plane (sometimes referred to the as the frontal plane). The height of the plane, i.e. position wherein the plane intersects the longitudinal axis, defines the size of the volumes containing the crow and root voxels. This method of splitting crown and root voxels may be most beneficial in the case of strictly employing a separate space containing the voxel representation of a crown as input to the deep neural network and a separate space containing the voxel representation of a root as output of deep neural network 210.

In another embodiment, both the input space and the output space of the deep neural network represent a voxel space that is capable of comprising the voxels that represent a complete tooth. In that case, the splitting may not necessarily be based on a plane. A more arbitrary (curved) split would more closely accommodate inputs as might be expected from voxel representation derived from an intra-oral scan. In such scan, the gum line, which is the boundary at which the segmentation would take place, is not expected to be straight.

When the crown is pointing upwards, the 'highest' position along the longitudinal axis where a plane normal to this axis would intersect an entire circumference of a segmented crown might be used. This plane may be used to split the voxels resulting in a 'straight' split. Such way of selecting crown voxels may however discharge a considerable amount of surface data of the segmented tooth, and thus information that may potentially be used by the deep neural network for accurate prediction of the root shape. Further details of the pre-processing are described hereunder in more detail with reference to FIG. 4.

The position of the normal plane along the longitudinal axis may be varied (within realistic boundaries) utilizing for example: the total tooth-height, an absolute distance and/or relative factor of this height (e.g. a quarter of the total height plus or minus a sixteenth, or a pre-determined height in millimetres, etc.), an expected height of a tooth that would not be obscured by the patient's gums, or any combination of such that can be automatically generated. During training, the same clinical 3D tooth data may be presented to the 3D deep neural network multiple times with variations in the position of the plane that determines the crown-root splitting thereby providing a 3D deep neural network training with improved robustness towards inputs.

In a further embodiment, the pre-processor 204 may also generate non-straight splits, e.g. simulating inputs as would be received being 3D crown models as resulting from segmenting intra-oral scans. In such case, the pre-processor may split the received 3D model data along a more curved surface, through at least a 3D reference point at a height that may be determined as described above and the centre of mass of the enclosing circumference of the surface at this height. Further, realistic limits regarding the amount of allowed curvature may be selected (e.g. a maximum height-difference between the highest and lowest point of the curved surface intersecting the received enclosed volume, a maximum allowed curvature, etc.). Also in this case, the same tooth may be presented multiple times to the input of the 3D deep neural network wherein each time a variation in the split height may be introduced allowing robustness of the trained neural network.

In another embodiment, the input of the pre-processor may be configured to receive 3D surface meshes resulting from optical scans of a complete clinical tooth. Such surface meshes may be pre-processed as described above, including transforming such surface meshes into a voxel representation which fits the input space of the deep neural network.

In a further embodiment, the training data 200 may be enhanced data from other more accurate sources. To that end, the clinical 3D data 202 may further comprise 3D data sets of 3D crown models, which may be derived from optically generated 3D data generated by an intra-oral scanner. Typically, the optically generated 3D data includes a 3D mesh comprising a plurality of 3D crown models of a dentition, which may be segmented and transformed by the pre-processor 204 into a plurality of optically generated 3D data sets. Each generated 3D data set may yield a highly accurate voxel representation of a 3D crown 208, which is formatted (in terms of size, position and orientation) for input to the deep learning network and which may be used for training the deep neural network.

Hence, in case for one 3D tooth model both an X-ray generated 3D data set and more accurate optically generated 3D data set are available, the deep neural network may be trained using a voxel representation of the crown which is derived from the optically generated 3D data set in combination with a voxel representation of the root which is derived from the X-ray generated 3D data set of the associated root model as (part of) a target. The use of optically generated 3D data of a crown model (a 3D mesh of a crown) for training may be beneficial in cases where the 3D crown data is derived from a relatively low-resolution 3D CBCT scan. In such case, the pre-processing may require an alignment step setting the location and orientation of the 3D data of the crown to match the crown section within the 3D image data of the full tooth.

The performance of the trained 3D deep learning network may be validated through the comparison of voxel representation of the predicted root 212 or full tooth 214 and the original (real-world) 3D image data 202, as illustrated below with reference to FIG. 6. In the case where inputs and outputs (target labels) of deep neural network 210 are strictly separated into a root section and a crown section, this validation may be done through comparison of the 3D image data of predicted root and the matching part of the original (real-world) 3D image data of the root.

Pre-processer 204 may facilitate augmentation of data by introducing relatively small transformations of the received 3D image data before the split is employed. Such transformation may e.g. consist of mirroring the 3D image data along a patient's sagittal plane, and/or relatively small rotations and re-scaling along either of the three orthogonal axis.

The training process as depicted in FIG. 2 results in a 3D deep neural network that is trained to accurately predict a 3D root shape on the basis of an arbitrary selected 3D crown such as a voxel representation of a crown derived from 3D data generated by an intra-oral scanner. The deep neural network will automatically learn the anatomical features available from the received voxel representation of the crown to generate an anatomically accurate prediction of (at least) a root representation, wherein the resulting root model will closely fit the crown model in order to form a full tooth model.

Due to the fact that such features can be learned from any potential training sample (a sample being the voxel representation of the crown), and that the 3D deep neural network will determine which features are relevant, the method has the ability to more accurately make use of any relevant information in said voxel representation. In other words, where prior art may be limited to a specific set of input parameters, the method proposed has the potential to make use of more input information and will determine which derivable features are relevant during training.

Additionally, the 3D deep neural network will learn a generalization of 3D image data representing root sections based on crown sections. This generalization is however more flexible (considering the potential different shapes that can be generated for either predicted root or complete tooth) than making use of a template root as is done in prior art. It is also worth to note that the method does not require separate input that indicates tooth classes (canine, molar, etc.) and/or patient classes (age, gender, etc.). In effect, the 3D deep neural network has the potential to recognize relevant features that are the result of such a classification directly from the received voxel representation. This is however (at least) dependant on the amount of available training samples, their variation across such classes, and memory bandwidth available within the feature representations in the 3D deep neural network.

Figure 3:
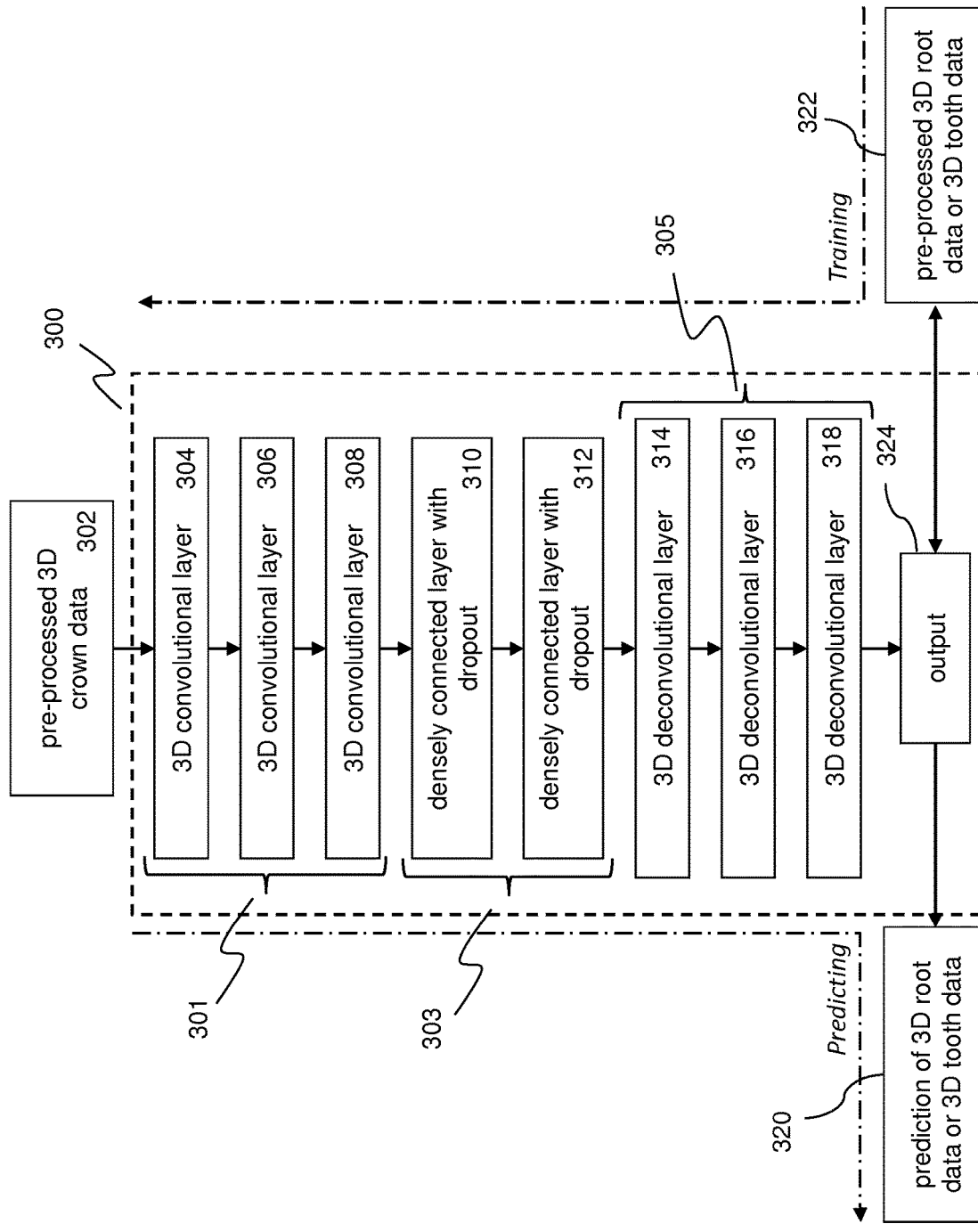
FIG. 3 depicts an example of a 3D deep neural network architecture for use in the methods and systems for automated root shape prediction from 3D crown image data according to an embodiment of the invention.

FIG. 3 depicts an example of a 3D deep neural network architecture 300 for use in the methods and systems for automated root shape prediction from 3D crown image data according to an embodiment of the invention. The received (pre-processed) 3D image data, e.g. a voxel representation that matches the voxel space of the input of the deep neural network, may be passed through and processed by a variety of (different types of) network layers forming the network. The architecture of the network may include three different functional sections 301,303,305.

A first section 301 may be configured to progressively encode features by means of 3D convolutional layers 304, 306,308. Such features are derived by learned (resulting from training) sets of 3D convolutional filters. Generated feature maps resulting from such layers will represent information that is relevant for the problem of root shape prediction. Stacking multiple 3D convolutional layers leads to an increase in the (potential) field of view per additional layer, as well as the ability to derive combined information from the previous layers derived information. In this respect, the input 302 may be considered as a first set of information.

Due to the nature of 3D convolutional layers, memory and processing requirements are comparatively lower then when e.g. making use of fully connected layers. For reasons of the desired accuracy of the predictions, there is a minimum size of the input (voxel) space. It is desirable however to also perform processing on information derived from the entire input space, e.g. by means of densely connected layers. For this reason, a reducing of the (3D) feature space size may be implemented, e.g. making uses of strides or subsampling within such 3D convolutional layers. Alternatively, the convolutional layers may be followed by a pooling layer, such as a max pooling layer well known in the art.

Hence, when the data have passed the convolutional layers, the internal representation may be passed to a series of densely-connected layers 310,312 which are configured to function as an intermediate for the inference of root shape selection from previous convolutional activations. The densely-connected layers may form a second section 303 of the network. Such layers, at this point in the neural network, have the ability of accessing derived information from the entire input space.

After the densely-connected layers, the resulting activations may be passed through a series of 3D de-convolutional layers 314,316,318 forming a third section 305 of the network. Such layers are also known as transposed convolutional layers. Parameters for such layers may be selected in such a way that the (3D) space represented at a point in the network architecture may be expanded. Again making use of such layers reduce the hardware (memory, processing speed) requirements required for realistically possible architectures and (timely) predictions. Alternatively, regular 3D convolutional layers may be employed, followed by (3D) up-sampling layers as are known in the art.

In an alternative embodiment, layers from section one are also directly connected to layers from section three. In this way the network, also known in the art as a U-network 'forwards' features maps from a compression stage (represented by section one) to a decompression stage (represented by section three). This can be done between results from convolutional layers, to de-convolutional layers, when each convolutional and deconvolutional set operates on at least the same encoded spatial resolution. This may improve quality of predictions and/or reduce time for training to converge to a desired accuracy. An example of a U-network architecture is described with reference to FIG. 11B.

Variations in the number of layers and their defining parameters, e.g. differing activation functions (e.g. sigmoid, tanh, elu, softmax), kernel (of filter) amounts and sizes, use of subsampling and dilation(s), and additional functional layers such as dropout layers may be used in the implementation without losing the essence of the design of the deep neural network. This same applies to varying parameter initiation methods as are known in the art. (E.g. (glorot) normal or uniform, He normal, etc.) The final or output layer 324 may result in individual voxel activations, wherein each voxel activation represents a probability measure defining the probability that a voxel is part of the 3D root or complete tooth. The voxel activations may be thresholded to obtain a binary prediction of root or complete tooth 3D data 320. In cases where the final layer employs a softmax activation (which is common for a classification problem), represented voxel activations higher than 0.5 for the class of 'tooth root' or 'complete tooth' are threshold to be binary '1' or 'True' representing that such voxel is predicted to be 'root' or 'tooth'. Alternatively, such binary attribution is done based upon an argmax over the to be predicted classes, effectively attributing the voxel with the most highly activated class. Thus, a voxel may be predicted to be part of the root or of the complete tooth class if the activation of such class is highest for such voxel.

Thus, in an embodiment, the first 3D deep neural network may include three sequential sections, the first section comprising at least a plurality of 3D convolutional layers configured such that the spatial resolution of derived information resulting from the section is reduced compared to the input resolution, the second section being configured to have the ability of processing all information resulting from the first section in parallel, preferably by means of densely connected layers, and the third section comprised of at least a plurality of 3D convolutional layers configured such that the spatial resolution of the resulting output of the total network is at least of the same resolution as the input resolution, preferably by means of transposed convolutions.

The network may be trained using training data as described with reference to FIG. 2. For each sample, a matching 3D representation of a single root or complete tooth may be used to determine a loss between desired 322 and actual output 320. This loss may be used during training as a measure to adjust parameters within the layers of the deep neural network. Optimizer functions may be used during training to aid in the efficiency of the training effort (e.g. stochastic gradient decent, rmsprop, adam, etc.). The network may be trained for any number of iterations until the internal parameters lead to a desired accuracy of results. When appropriately trained, a voxel representation containing at least a representation of a tooth crown may be presented as input and the deep neural network and may be used to derive a prediction of a voxel representation of a corresponding 3D root or complete tooth.

FIGS. 4A and 4B depict schematics of pre-processing and post-processing 3D data according to various embodiments of the invention. In particular, FIG. 4A depicts a flow-diagram of a process executed by a pre-processor. In a first step 402 the pre-processor may derive individual 3D crown data from 3D data originating from different sources, e.g. CBCT data of a dento-maxillofacial structure or 3D surface meshes of a dentition generated by an intra-oral scanner. In such cases, the pre-processing may include the execution of a segmentation process in which the 3D data received by the pre-processor are segmented in individual 3D crown data. In case of 3D CBCT data, the segmentation process may be executed by a separate neural network, which classifies voxels into a particular voxel type, e.g. a voxel representing part of a tooth, and form a 3D data set of a tooth of the a dento-maxillofacial structure. An example of such segmentation process is described below with reference to FIG. 8 and further. In case the 3D data comprises a 3D mesh representing a dentition generated by an intra-oral scanner, the pre-processor may include a segmentation process wherein the 3D mesh of the dentition is segmented into individual 3D meshes of crowns.

Thereafter, the pre-processor may transform the individual 3D tooth data in a voxel representation of the crown (step 404). Hence, in case of a 3D surface mesh, the 3D mesh may be transformed into a volume of voxels. An interpolation algorithm may be used in order to fill the voxel space with voxels, including voxels that have predetermined first voxel value, e.g. a 'zero' or 'background' value, where no tooth surface is present, and a second voxel value 'one' or 'tooth present' value for those voxels that coincide or almost coincide with the 3D surface defined by the meshes. In case of a voxel representation of a complete tooth a voxel representation of crown data may be determined by splitting the data of the full tooth into crown data and root data as described with reference to FIG. 2. The voxel representation thus includes a volume, e.g. a rectangular box, of voxels wherein the 3D surface of a crown is represented by voxels within the volume.

In an embodiment, the pre-processor may also execute the step 406 of setting voxels enclosed by the surface mesh to the second voxel value, so that the 3D voxel representation represents a solid object in a 3D space. It is noted that the enclosing surface of a voxel representation of e.g. a partial crown may not yet be a fully enclosed surface (as may e.g. be the case when a voxel representation of a tooth is split into a crown and a root section, or when a voxel representation of a crown is based on the segmentation of a 3D mesh generated by an intra-oral scan). In case during training a voxel representation of a tooth is split along a plane into a volume of crown voxels and a volume of root voxels (see also FIG. 2 above), step 406 may include closing the volume and determine the solid representation by creating faces within the splitting plane, enclosing the already existing surface.

In the case the edges of such voxel representation are not in the same plane, step 406 may include a determining 3D point that would be the centre of mass of the 'highest' surface (in a real-world 'up-down' direction, wherein the crown-side of the tooth is oriented 'up'), the surface being defined from the highest available fully closed circumference as intersecting a plane normal to said 'up-down' direction. The original (split) volume may then be closed by creating faces defined by the determined 3D point (being within the volume as would be enclosed by the original received surface), and the vertices along the open edge of the original received surface. Due to the nature of teeth shapes, this method would close and fill the open surface in a way that would guarantee that the resulting volume is indeed (part of) the tooth volume in the real-world. In some embodiments, the received 3D crown model may already be enclosed, as would be the case for models generated by e.g. segmentation from CBCT data, as described further below with reference to FIG. 8.

In an embodiment, the (rectangular) volume of voxels may be associated with a coordinate system, e.g. a 3D Cartesian coordinate system so that the 3D voxel representation of a tooth may be associated with an orientation and dimension. The orientation, position and/or dimensions of the teeth models however may not be standardized. A 3D deep neural network may sensitive to the orientation of the tooth and may have difficulties predicting a root shape from a random crown orientation and non-standardized dimensions in the 3D image volume. Hence, it may be beneficial to present the 3D deep neural network (both during training and inference) with voxel representations in which the dimensions of the voxels (i.e. the real-world length, width and height of the space represented by the voxel) are the same for every presented sample or representation. Additionally, it may be beneficial to present the 3D deep neural network (both during training and inference) with voxel representations in which the orientation, position and dimensions of the tooth samples are the same for every sample.

In order to address this problem, during the pre-processing of the 3D input data, the orientation, position and dimensions of the individual crown samples may be normalized in accordance with a normalization that was used in order to normalize the training data. The pre-processer may ensure that voxels representing a crown (i.e. a voxel representation as described above with reference to steps 404 and/or 406), may be transformed using e.g. a canonical transformation such that the orientation, position and dimensions of the transformed samples are uniform and normalized (step 410). The pre-processor may accomplish such normalization of the orientation, position and/or dimensions using spatial information of the 3D data sources. In an embodiment, the spatial information may be determined by the pre-processor by examining the orientation, position and dimensions of the data source (step 408). For example, when crown samples originate from a 3D (CB)CT data stack defining a volume of voxels, or from an intra-oral scan, the orientation, position and dimensions of each tooth or crown sample may be determined by the system.

The pre-processor may examine the orientation, position and/or dimensions derived from the original 3D image data set and if these values do not match the desired (normalized) input format for the deep learning network, a transformation may be applied. In an embodiment, the transformation may include a 3D rotation for re-orienting the orientation of a sample in the 3D space. The reorientation may result in a (normalized) orientation expected by the neural network (step 410 which is described in more detail above with reference to feature 102). In an embodiment, the transformation may include a 3D translation for repositioning the sample in the 3D space. The repositioning ensures (normalized) positioning of a 3D crown model within any space size as expected by the 3D neural network. In yet another embodiment, the transformation may include 3D scaling for re-scaling the dimensions of a sample in the 3D space (step 412). The rescaling ensures (normalized) dimensions of a sample as expected by the 3D neural network.

In an embodiment, (part of) the pre-processor may include a (third) deep neural network that is trained to perform the transformation as described above. In an embodiment, the trained neural network as described in European patent application no. 18181421.1, with title "Automated determination of a canonical pose of a 3D dental structure and superimposition of 3D dental structures using deep learning", which is hereby incorporated by reference into this application.

FIG. 4B depicts a flow-diagram of a process executed by a post-processor. In an embodiment, the post-processor may combine (merge) the voxel representation of a crown 414 and a voxel representation of a root shape 416 generated by the 3D deep neural network in a merged voxel representation of a complete tooth 420. In an embodiment, the merged voxel representation may be transformed into a 3D mesh of the complete tooth 422. Alternatively, the post-processor may transform the voxel representation of the root shape into a 3D mesh and combine (merge) the 3D mesh representation of the root shape with the 3D mesh representation of the crown. In yet another embodiment, the 3D deep neural network may generate a voxel representation of a complete tooth 418, and the post-processor may directly transform the output of the 3D deep neural network into a 3D mesh of the complete tooth.

Figure 5A:
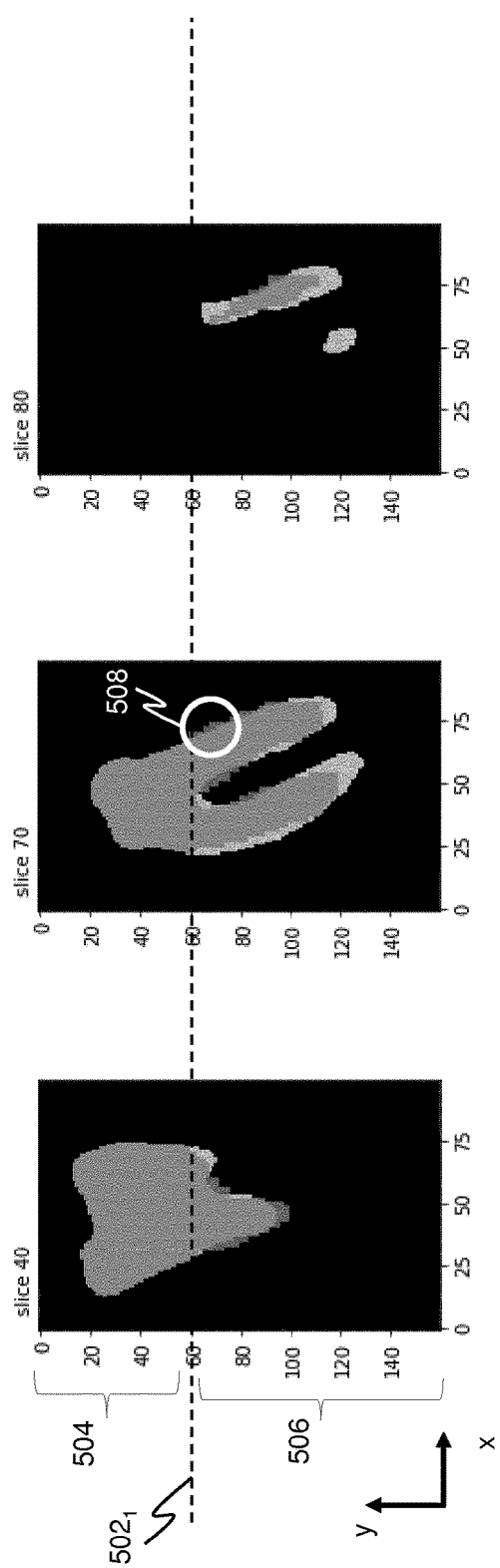
FIG. 5A and FIG. 5B show illustrations of the 3D clinical voxel representation compared to the predicted voxel representation.
Figure 5B:
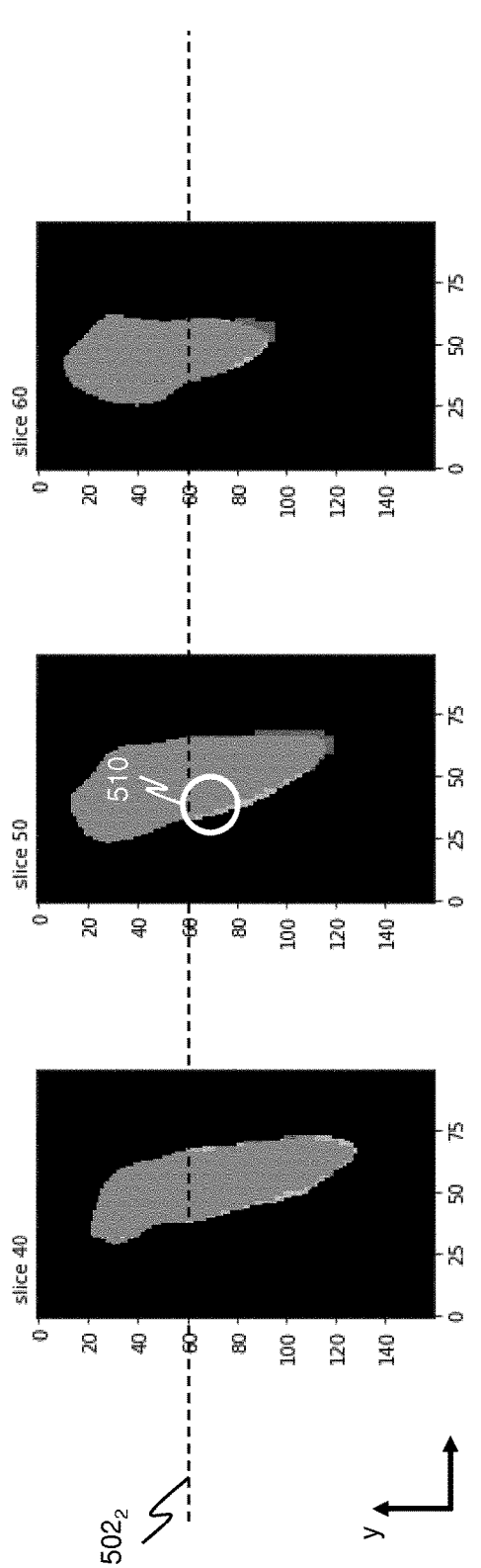

FIG. 5A and FIG. 5B show illustrations of the 3D clinical voxel representation compared to the predicted voxel representation. FIG. 5A is an example of a 'molar' type tooth, and FIG. 5B of a 'canine' type tooth. (Both are held-out samples, or samples not used during training). The representations were rendered in a voxel space defining a volume of 160×100×100 voxels (in a x,y,z coordinate system). The x and y-axis as visualised compose a patient's coronal plane. The slice numbering above the figure indicates a distance along the z-axis at which point the slice is visualised. For example, FIG. 5A depicts three slices (in the x-y plane) of the voxel space at three different positions on the z-axis. These illustrations provide a clear indication about the accuracy of the root shape that is predicted by the 3D deep neural network. Voxel size in the case of these illustrations is 0.2 mm in each orthogonal direction.

The predicted tooth is illustrated as the resulting merger of the voxel representation of a crown that was offered to the input of the system and a predicted root in the voxel space containing a complete tooth. Each figure comprises a slice of a representation of the clinical 3D model and a slice of the complete predicted 3D model of the tooth, which is placed over the clinical 3D model. The thus formed figures illustrate the overlap between the clinical root shape and the predicted root shape in a medium shade of grey, wherein the lighter shade of grey (representation of clinical tooth present but not the representation of the predicted tooth) and the darker shade of grey (representation of clinical tooth not present but the representation of the predicted tooth present)

indicate the parts in which the predicted representation deviates from the clinical representation.

The split employed for training and prediction in the case of this exemplary embodiment made use of a 'straight' split, as shown by lines $502_1$ and $502_2$ (which represent a plane in the x-z direction). Hence, the upper (first) part 504 of the volume defines voxels representing the crown that were used as input to the deep neural network. The lower part 506 defines voxels that were predicted by the neural network on the basis of the input. Hence, in this example, the voxel space of the input of the deep neural network represents a volume of 60×100×100 voxels and the voxel space of the output of the deep neural network represents a volume of 100×100×100 voxels. More details on the exemplary system used for generation of these results are described below with reference to FIG. 6.

Due to the nature of the processing performed by the deep neural network, hard transition edges between the original crown section and the predicted root section are not present, as might be the case when employing a system utilizing template 3D models such as in prior art. The transitions between the original crown section and the predicted root section as learned by the system and hence predicted are considered as a smooth transition (see e.g. 508, 510) with little to no necessity for additional post-processing, e.g. smoothing or the like. The illustrations also show the accuracy throughout the predicted 3D image data. The predicted root sections overlap to a large extent with the clinical tooth. More detailed information considering this accuracy can be found with respect to FIG. 6. It is however noteworthy looking at these illustrations that the shown predicted 3D root sections (everything below lines $502_1$ or $502_2$ for respectively FIG. 5A or 5B) are automatically predicted by the system based the information above these same lines.

FIG. 6A and FIG. 6B show tables of Dice coefficients as determined from the same exemplary embodiment with reference to FIGS. 5A and 5B. In more detail, these are results on a held-out set of teeth (meaning these teeth were not part of the training set), comparing a voxel representation of the actual 3D clinical teeth to the voxel representation of the 3D complete teeth as predicted by a single trained 3D deep neural network, employing a voxel size of 0.2 mm in each dimension. A 'straight' split between crown and root was employed, with a separated input and output voxel space. Some 900 3D clinical teeth models as derived from CBCT scans were used for training, additionally making use of augmentation of the 3D image data.

This training data contained a variety of tooth classes, including incisors, canines, premolars and molars. For the purpose of the example the Dice coefficients in FIG. 6A are shown divided into these classes. The table in FIG. 6B shows the same total set of results aggregated into a different set of classes, namely aggregated per individual tooth type as can be found within a dentition and according to the FDI World Dental Federation Notation. It is emphasized however that all results are generated by a single 3D deep neural network. A Dice coefficient or Dice score is a measure of similarity of objects. This parameter is commonly used in image segmentation to compare a predicted result to a ground truth (in the case of this system the 3D clinical teeth). A Dice score can be described as the size of the overlap between two objects (in this case taken on a per-voxel level) divided by the total size of the two objects. This metric takes into account true positives, total positives and false positives, with a higher score representing a more accurate result.

As shown by the results in FIG. 6A, the class of premolars in general is the 'least accurate' on average (in this case meaning with the lowest Dice coefficient) when comparing the prediction to the clinical 3D models (or ground truth) of teeth. Note however that the table only shows results of an exemplary embodiment. The set of held-out samples has been randomly selected and a different selection will lead to different results. (This can also be seen in FIG. 6B where it is apparent that tooth indices 18, 38 and 48 were not present in the randomly selected held out data set) Also, the exact 3D deep neural network architecture and parameters used within such network, training considerations such as the selection of the in- and output space size, augmentation options during training, etc. may influence the accuracy of prediction results. When employing a larger dataset of training samples, the accuracy and Dice score are expected to become higher.

Figure 7:
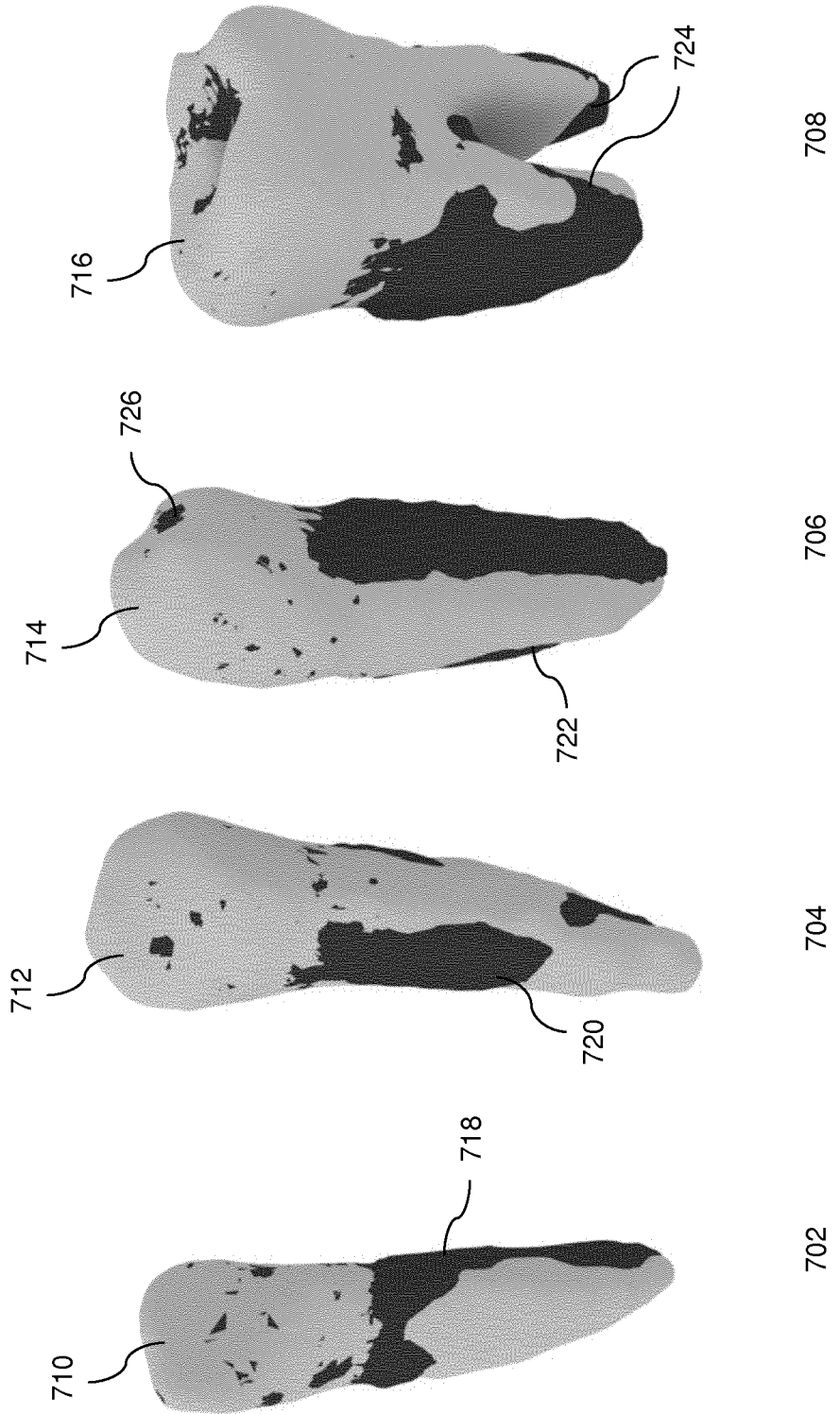
FIG. 7 shows visualisations illustrating 3D models of clinical teeth combined with prediction results.

FIG. 7 illustrates 3D models of clinical teeth as generated by a system according an embodiment of the invention. In particular, FIG. 7 illustrates 3D models of clinical teeth which are combined with predictions of a complete tooth, having only received a crown section. These are results from the same exemplary embodiment as described with reference to FIGS. 5 and 6 above. Illustrated are single examples from four different classes of teeth (incisor 702, canine 704, pre-molar 706 and molar 708), being determined by the system that includes the trained 3D deep neural network. These illustrations are rendered based on individual 3D models, i.e. 3D meshes, of a whole tooth that are generated on the basis of a voxel representation of a predicted root as described above. The original 3D clinical teeth models are rendered in lighter grey and the 3D tooth models generated on the basis of a predicted voxel representation of a tooth are rendered in the darker shade. Each generated 3D tooth model is overlaying its original 3D clinical tooth model in order to provide a visual comparison of the results. It is again worthy to note that these are held-out samples. In the visualisation of FIG. 7, some patches of darker grey are visible at the crown sections (726). This is the result of overlaying the original 3D clinical tooth model and the 3D model of the complete predicted tooth, the latter having gone through the step of merging a predicted root voxel representation with the voxel representation of the received crown. Where such patches are visible, the render engine may have determined that the surface of the 3D predicted complete tooth is the slightest fraction 'higher' on the surface, hence the darker shade of the predicted tooth is visible. The comparison with the original 3D clinical crown models (710 to 716) shows that the trained deep learning network is capable of generating an accurate prediction of the root shape (718 to 724), including (were applicable) the amount of roots (724).

As described above, in some embodiments the 3D data that is offered to the input of the system may represent a dento-maxillofacial structure, including voxels related to (parts of) the jaw bone, the teeth and the nerves. In those embodiments, segmentation of the dento-maxillofacial structure into separate parts, e.g. jaw bone and individual tooth. is required in order to determine a 3D voxel representation of individual teeth crowns that can be used by 3D deep learning network. Additionally, for the purpose of training the 3D deep learning network, a large number of full tooth shapes may be required in order to learn the deep neural network to predict a root shape based on a crown shape. Automatic segmentation of 3D teeth from CBCT scans would prove very beneficial considering the availability and relative ease of creating such CBCT scans. Hence, in those cases, the invention also includes computer systems and computer-implemented methods that use 3D deep neural networks for classifying, segmenting and 3D modelling the individual teeth of a dentition in a dento-maxillofacial structure, wherein the dento-maxillofacial structure is represented by 3D image data defined by a sequence of images forming a CT image data stack, in particular a cone beam CT (CBCT) image data stack. The 3D image data may comprise voxels forming a 3D image space of a dento-maxillofacial structure.

Such computer system according to the invention may comprise at least one 3D deep neural network which is trained to classify a 3D image data stack of a dento-maxillofacial structure into voxels of different classes, wherein each class may be associated with a distinct part (e.g. teeth, jaw, nerve) of the structure. The computer system may be configured to execute a training process which iteratively trains (optimizes) one or more deep neural networks on the basis of one or more training sets which may include accurate 3D models of dento-maxillofacial structures. These 3D models may include optically scanned dento-maxillofacial structures (teeth and/or jaw bone). Once trained, the deep neural network may receive a 3D image data stack of a dento-maxillofacial structure and classify the voxels of the 3D image data stack. Before the data is presented to the trained deep neural network, the data may be pre-processed so that the neural network can efficiently and accurately classify voxels. The output of the neural network may include different collections of voxel data, wherein each collection may represent a distinct part e.g. teeth or jaw bone of the 3D image data. The classified voxels may be post-processed in order to reconstruct an accurate 3D model of the dento-maxillofacial structure.

The computer system comprising a trained neural network for automatically classifying voxels of dento-maxillofacial structures, the training of the network, the pre-processing of the 3D image data before it is fed to the neural network as well as the post-processing of voxels that are classified by the neural network are described hereunder in more detail.

Figure 8:
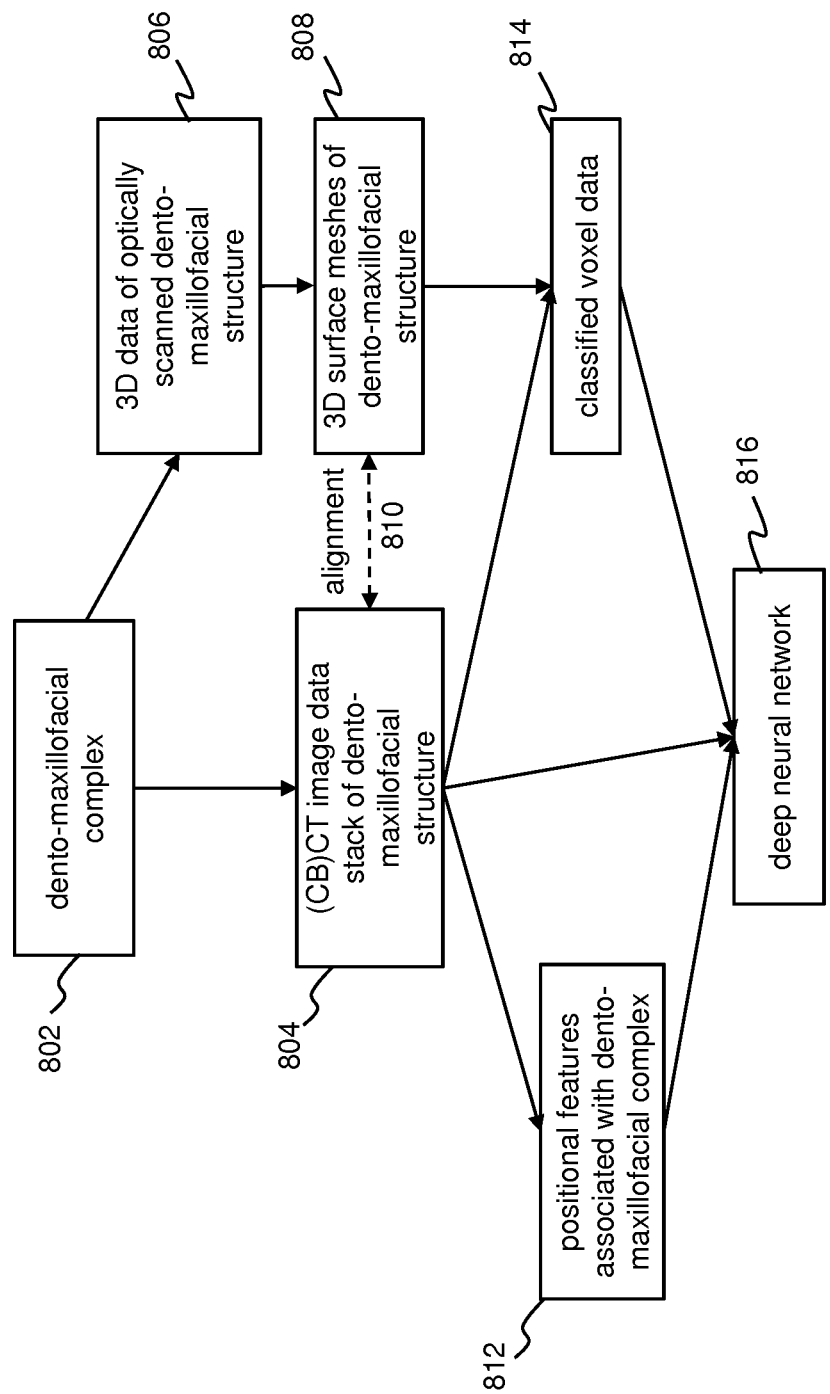
FIG. 8 schematically depicts a computer system for classification and segmentation of 3D dento-maxillofacial structures according to an embodiment of the invention.

FIG. 8 depicts a flow diagram of training a deep neural network for classifying dento-maxillofacial 3D image data according to an embodiment of the invention. Training data is used in order to train a 3D deep learning neural network so that it is able to automatically classify voxels of a 3D CT scan of a dento-maxillofacial structure. As shown in this figure, a representation of a dento-maxillofacial complex 802 may be provided to the computer system. The training data may include a CT image data stack 804 of a dento-maxillofacial structure and an associated 3D model, e.g. 3D data 806 generated by optical scanning of the same dento-maxillofacial structure. Such 3D data may be referred to as 3D optical scanning data. Examples of such 3D CT image data and 3D optical scanning data are shown in FIGS. 9A and 9B. FIG. 9A depicts DICOM slices associated with different planes of a 3D CT scan of a dento-maxillofacial structure, e.g. an axial plane 902, a frontal or coronal plane 904 and the sagittal plane 906. FIG. 9B depicts 3D optical scanning data of a dento-maxillofacial structure. The computer may form 3D surface meshes 808 of the dento-maxillofacial structure on the basis of the optical scanning data. Further, an alignment function 810 may be employed which is configured to align the 3D surface meshes to the 3D CT image data. After alignment, the representations of 3D structures that are provided to the input of the computer use the same spatial coordinate system. Based on the aligned CT image data and 3D surface meshes positional features 812 and classified voxel data of the optically scanned 3D model 814 may be determined. The positional features and classified voxel data may than be provided to the input of the deep neural network 816, together with the image stack 804.

Hence, during the training phase, the 3D deep learning neural network receives 3D CT training data and positional features extracted from the 3D CT training data as input data and the classified training voxels associated with the 3D CT trainings data are used as target data. An optimization method may be used to learn the optimal values of the network parameters of the deep neural network by minimizing a loss function which represents the deviation the output of the deep neural network to the target data (i.e. classified voxel data), representing the desired output for a predetermined input. When the minimization of the loss function converges to a certain value, the training process could be considered to be suitable for application. The training process depicted in FIG. 8 using 3D positional features in combination with the training voxels, which may be (at least partly) derived from 3D optically scanning data, provides a high-quality training set for the 3D deep learning neural network. After the training process, the trained network is capable of accurately classifying voxels from a 3D CT image data stack.

Figure 10A:
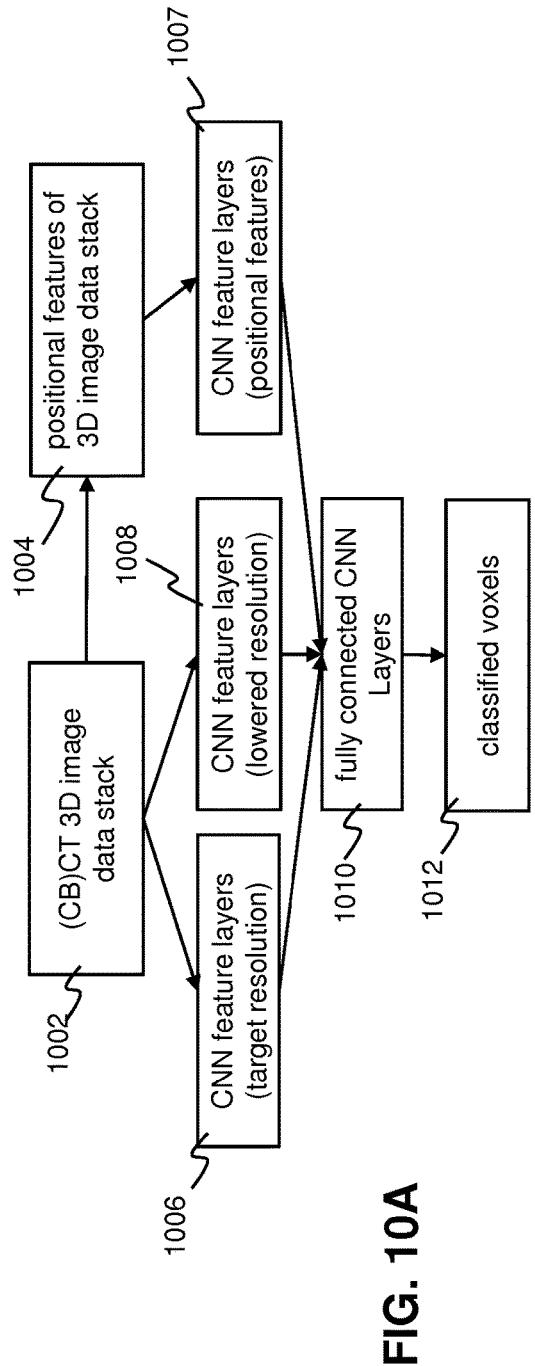
FIGS. 10A and 10B depict examples of deep neural network architectures for classifying dento-maxillofacial 3D image data.
Figure 10B:
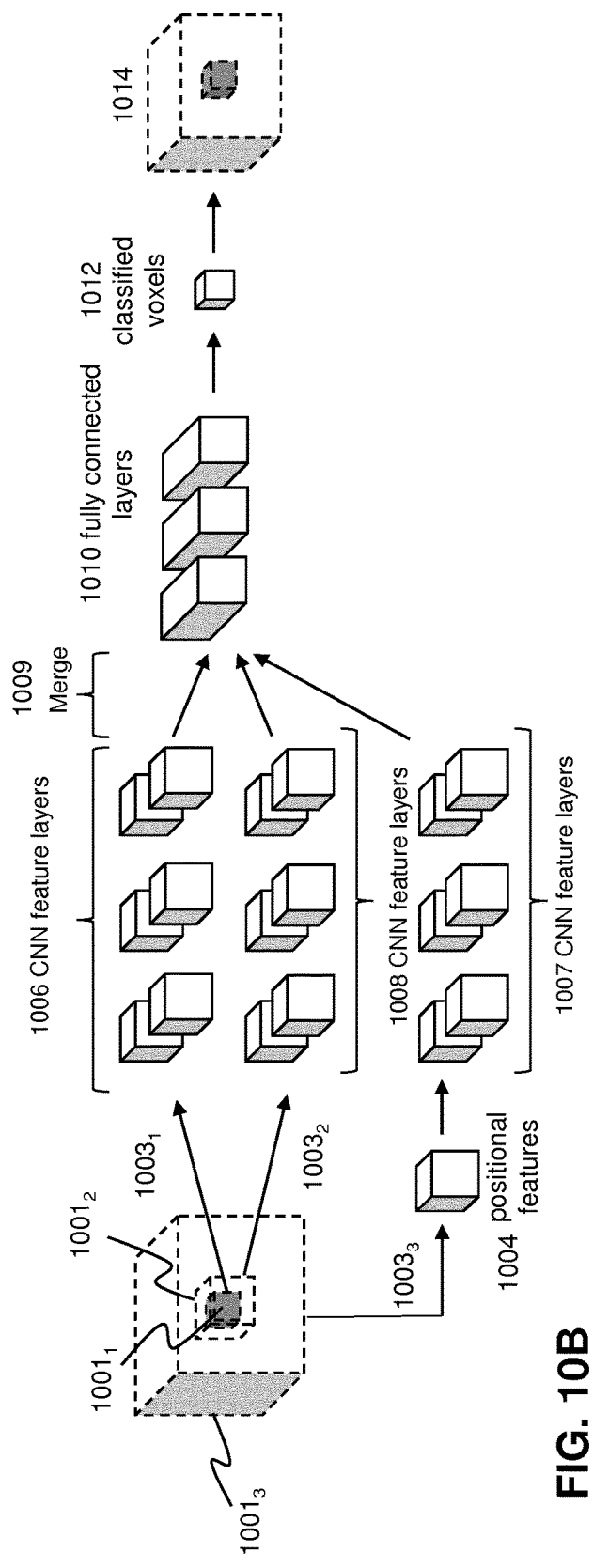

FIGS. 10A and 10B depict high-level schematics of deep neural network architectures for use in the methods and systems that are configured to classify and segment 3D voxel data of a dento-maxillofacial structure. The deep neural networks may be implemented using one or more 3D convolutional neural networks (3D CNNs). The convolutional layers may employ an activation function associated with the neurons in the layers such as a sigmoid function, tanh function, relu function, softmax function, etc. A deep neural network may include a plurality of 3D convolutional layers wherein minor variations in the number of layers and their defining parameters, e.g. differing activation functions, kernel amounts and sizes, and additional functional layers such as dropout and batch normalization layers may be used in the implementation without losing the essence of the design of the deep neural network.

As shown in FIG. 10A, the network may include a plurality of convolutional paths wherein each convolutional path is associated with a set of 3D convolutional layers. In an embodiment, the network may include at least two convolutional paths, a first convolutional path associated with a first set of 3D convolutional layers 1006 and a second convolutional path associated with a second set of 3D convolutional layers 1008. The first and second convolutional paths may be trained to encode 3D features derived from received 3D image data associated with the voxels that are offered to the input of the first and second convolution paths respectively. Further, in some embodiments, the network may include at least a further (third) convolutional path associated with a third set of 3D convolutional layers 1007. The third convolutional path may be trained to encode 3D features derived from received 3D positional feature data associated with voxels that are offered to the input of the third path.

Alternatively, in another embodiment, instead of a further convolution path that is trained on the basis of 3D positional feature data, the 3D positional feature data also associated with the intensity values of voxels that are offered to the input of the first and second convolution paths. Hence, in this embodiment, the first and second convolutional paths may be trained based on training data including a 3D data stack of voxel values including intensity values and positional feature information.

The function of the different paths is illustrated in more detail in FIG. 10B. As shown in this figure, voxels are fed to the input of the neural network. These voxels are associated with a predetermined volume, which may be referred to as the image volume $1001_3$. The total volume of voxels may be divided in first blocks of voxels and 3D convolution layers of the first path $1003_1$ may perform a 3D convolution operation on each of the first blocks of voxels $1001_1$ of the 3D image data. During the processing, the output of each 3D convolution layer may be the input of a subsequent 3D convolution layer. This way, each 3D convolutional layer may generate a 3D feature map representing features of the 3D image data that are fed to the input. A 3D convolutional layer that is configured to generate such feature maps may therefore be referred to as a 3D CNN feature layer.

As shown in FIG. 10B, the convolutional layers of the second convolutional path $1003_2$ may be configured to process second blocks of voxels $1001_2$ of the 3D image data. Each second block of voxels is associated with a first block of voxels, wherein the first and second block of voxels have the same centered origin in the image volume. The volume of the second block is larger than the volume of the first block. Moreover, the second block of voxels represents a down-sampled version of an associated first block of voxels. In other words, the voxel resolution of the second block is lower than the voxel resolution of the associated first block. The down-sampling factor may be any appropriate value. In an embodiment, the down-sampling factor may be selected between 20 and 2, preferably between 10 and 3.

Hence, the 3D deep neural network may comprise at least two convolutional paths. A first convolutional path $1003_1$ may define a first set of 3D CNN feature layers (e.g. 5-20 layers), which are configured to process input data (e.g. first blocks of voxels at predetermined positions in the image volume) at a first voxel resolution, e.g. the voxel resolution of the target (i.e. the resolution of the voxels of the 3D image data to be classified). Similarly, a second convolutional path may define a second set of 3D CNN feature layers (e.g. 5-20 layers), which are configured to process input data at a second voxel resolution (e.g. second blocks of voxels wherein each block of the second blocks of voxels $1001_2$ has the same center point as its associated block from the first block of voxels $1001_1$). Here, the second resolution is lower than the first resolution. Hence, the second blocks of voxels represent a larger volume in real-world dimensions than the first blocks. This way, the second 3D CNN feature layers process voxels in order to generate 3D feature maps that includes information about the (direct) neighborhood of associated voxels that are processed by the first 3D CNN feature layers.

The second path thus enables the neural network to determine contextual information, i.e. information about the context (e.g. its surroundings) of voxels of the 3D image data that are presented to the input of the neural network. By using multiple (parallel) convolutional paths, both the 3D image data (the input data) and the contextual information about voxels of the 3D image data can be processed in parallel. The contextual information is useful for classifying a dento-maxillofacial structures, which typically include closely packed dental structures that are difficult to distinguish, especially in case of CBCT image data.

In an embodiment, the neural network of 10B may further include a third convolutional path $1003_3$ of a third set of 3D convolutional layers which are trained to process specific representations of 3D positional features 1004 that may be extracted from the 3D image data. Extraction of the 3D positional features from the 3D image data may be realized as a pre-processing step. In an alternative embodiment, instead of using a third convolutional path for processing 3D positional features, the 3D positional information, including 3D positional features, may be associated with the 3D image data that is offered to the input of the deep neural network. In particular, a 3D data stack may be formed in which each voxel is associated with an intensity value and positional information. Thus, the positional information may be paired per applicable received voxel, e.g. by means of adding the 3D positional feature information as additional channels to the received 3D image information. Hence, in this embodiment, a voxel of a voxel representation of a 3D dento-maxillofacial structure at the input of the deep neural network may not only be associated with a voxel value representing e.g. a radio intensity value, but also with 3D positional information. Thus, in this embodiment, during the training of the convolutional layers of the first and second convolutional path both, information derived from both 3D image features and 3D positional features may be encoded in these convolutional layers.

The output of the sets of 3D CNN feature layers are then merged and fed to the input of a set of fully connected 3D CNN layers 1010, which are trained to derive the intended classification of voxels 1012 that are offered at the input of the neural network and processed by the 3D CNN feature layers.

The sets of 3D CNN feature layers are trained (through their learnable parameters) to derive and pass on the optimally useful information that can be determined from their specific input, the fully connected layers encode parameters that will determine the way the information from the previous paths should be combined to provide optimally classified voxels 1012. Thereafter, classified voxels may be presented in the image space 1014. Hence, the output of the neural network are classified voxels in an image space that corresponds to the image space of the voxels at the input.

Here, the output (the last layer) of the fully connected layers may provide a plurality of activations for each voxel. Such a voxel activation may represent a probability measure (a prediction) defining the probability that a voxel belongs to one of a plurality of classes, e.g. dental structure classes, e.g. a tooth, jaw and/or nerve structure. For each voxel, voxel activations associated with different dental structures may be thresholded in order to obtain a classified voxel.

FIG. 11-13 illustrate methods of determining 3D positional features in a 3D image data stack representing a 3D dento-maxillofacial structure and examples of such positional features. Specifically, in the case of manually engineered features both the 3D image data stack and the associated 3D positional features are offered as input to the 3D deep neural network so that the network can accurately classify the voxels without the risk of overfitting. A conversion based on real-world dimensions ensures comparable input irrespective of input image resolution.

A manually engineered 3D positional feature may provide the 3D deep neural network information about positions of voxels in the image volume relative to a reference plane or a reference object in the image volume. For example, in an embodiment, a reference plane may be an axial plane in the image volume separating voxels associated with the upper jaw and voxels with the lower jaw. In another embodiment, a reference object may include a curve, e.g. a 3D curve, approximating at least part of a dental arch of teeth in the 3D image data of the dento-maxillofacial structure. This way, the positional features provide the first deep neural network the means to encode abstractions indicating a likelihood per voxel associated jaw, teeth and/or nerve tissues in different positions in the image volume. These positional features may help the deep neural network to efficiently and accurately classify voxels of a 3D image data stack and are designed to reduce the risk of overfitting.

In order to determine reference planes and/or reference objects in the image volume that are useful in the classification process, the feature analysis function may determine voxels of a predetermined intensity value or above or below a predetermined intensity value. For example, voxels associated with bright intensity values may relate to teeth and/or jaw tissue. This way, information about the position of the teeth and/or jaw and the orientation (e.g. a rotational angle) in the image volume may be determined by the computer. If the feature analysis function determines that the rotation angle is larger than a predetermined amount (e.g. larger than 15 degrees), the function may correct the rotation angle to zero as this is more beneficial for accurate results.

FIG. 11A illustrates an example of a flow diagram 1102 of a method of determining manually engineered 3D positional features in a 3D image data 1104, e.g. a 3D CT image data stack. This process may include determining one or more 3D positional features of the dento-maxillofacial structure, wherein one or more 3D positional features being configured for input to the 3D deep neural network (as discussed with reference to FIG. 10B above). A manually engineered 3D positional feature defines position information of voxels in the image volume with respect to reference planes or reference objects in the image volume, for example, a distance, e.g. a perpendicular distance, between voxels in the image volume and a reference plane in the image volume which separates the upper jaw from the low jaw. It may also define distance between voxels in the image volume and a dental reference object, e.g. a dental arch in the image volume. It may further define positions of accumulated intensity values in a second reference plane of the image volume, an accumulated intensity value at a point in the second reference plane including accumulated intensity values of voxels on or in the proximity of the normal running through the point in the reference plane. Examples of 3D positional features are described hereunder.

In order to determine a reference object that provides positional information of the dental arch in the 3D image data of the dento-maxillofacial structure. A fitting algorithm may be used to determine a curve, e.g. a curve that follows a polynomial formula, that fits predetermined points in a cloud of points of different (accumulated) intensity values. In an embodiment, a cloud of points of intensity values in an axial plane (an xy plane) of the image volume may be determined. An accumulated intensity value of a point in such axial plane may be determined by summing voxel values of voxels positioned on the normal that runs through a point in the axial plane. The thus obtained intensity values in the axial plane may be used to find a curve that approximates a dental arch of the teeth.

Figure 11B:
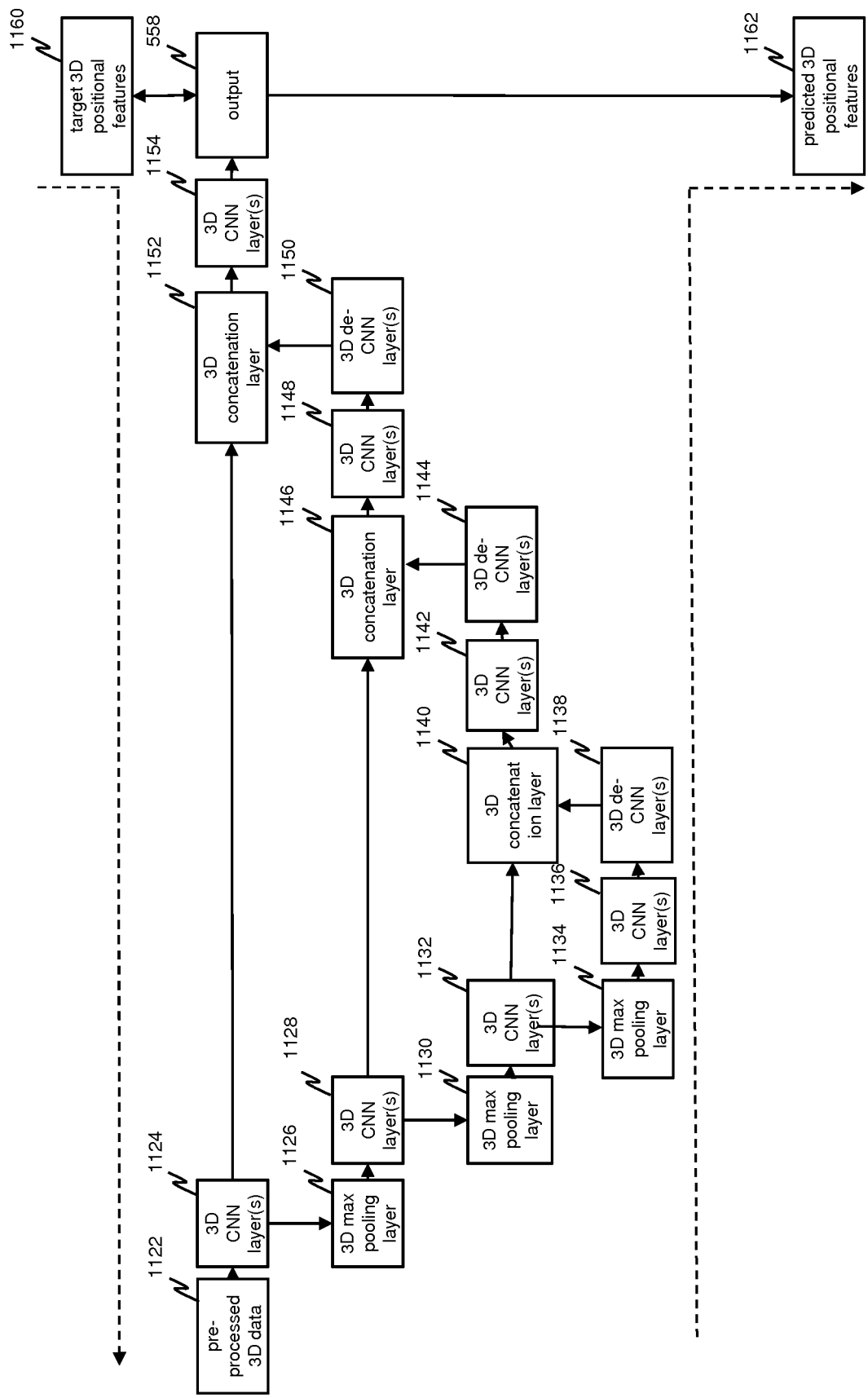

FIG. 11B depicts an example of a machine learning method as may be utilized to generate (non-manually engineered) relevant 3D positional features according to an embodiment of the invention. In particular, FIG. 11B depicts an exemplary 3D deep neural network architecture as may be trained to generate desired features to be processed by the segmentation 3D neural network. After training, such trained model may be employed analogous to method 502 as a pre-processor that derives relevant 3D positional features based on the entire received 3D data set.

Similar to manually engineered 3D positional features, the aim is to incorporate into the 3D positional features information regarding the entire received 3D data set (or at least a substantial part thereof) for use in the segmentation 3D deep learning network that is potentially relevant for the task of automated classification and segmentation, and may not otherwise be available from the set or sets of subsamples offered to the segmentation 3D deep learning network. Again, as with the manually engineered 3D positional features, such information should be made available per voxel in the received 3D data set.

One of the possible ways to implement such machine learning method for automatically generating 3D positional features is a trained deep neural network. Such network may be trained to derive 3D positional features on the basis of an input 3D data set (e.g. a voxel representation of a dento-maxillofacial structure) that is offered to the input of the 3D segmentation deep neural network. In an embodiment, the pre-processing deep neural network may be a 3D U-net type deep neural network as illustrated by FIG. 11B. Due to the limits of processing available (mostly memory requirements), such an architecture would not operate on the resolutions of the received voxel representations. Therefore, a first input 3D data set, a first voxel representation of a first resolution (e.g. 0.2×0.2×0.2 mm per voxel) may be down sampled to a second voxel representation of a second lower resolution, e.g. a resolution of 1×1×1 mm per voxel, using an interpolation algorithm. Thereafter, a 3D deep neural network that is trained on the basis of voxel representations of the second resolution may generate per input voxel 3D positional feature information. An interpolation algorithm may be used to scale this information up to the original first resolution. This way the resulting 3D positional features (spatially) coincide with the voxels of the first voxel representation yielding relevant information for each voxel of the first input 3D data set whilst taking into account information considering (an aggregated version of) the entire received 3D data set.

Such pre-preprocessing 3D deep neural network may be trained to approximate desired target values (being the desired 3D positional features). In this specific example the targets may for instance be a class indication per voxel on the resolution at which the pre-processing 3D deep neural network operates. Such class indications may for instance be sourced from the same pool of classified training voxels 136, but down-sampled in the same manner as the received 3D data set has been down-sampled. It is noted that such pre-processing machine learning method may effectively be considered as a coarse pre-segmentation, specifically one that potentially has access to information from the entire (or a substantial part of the) received 3D voxel representation. Pairing the rough pre-segmentation information to the applicable voxels of the received 3D image space, e.g. by means of upscaling, leads to these 3D positional features being processed in parallel with the received 3D image data, towards an outcome at the received 3D image resolution.

The pre-processing network may be implemented using a variety of 3D neural network layers, such as convolutional layers (3D CNNs), 3D max-pooling layers, 3D deconvolutional layers (3D de-CNNs), and densely connected layers. The layers may use a variety of activation functions such as linear, tanh, ReLU, PreLU, sigmoid, etc. The 3D CNN and de-CNN layers may vary in their number of filters, filter sizes and subsampling parameters. The 3D CNN and de-CNN layers, as well as the densely-connected layers, may vary in their parameter initialization methods. Dropout and/or batch normalisation layers may be employed throughout the architecture.

Following a 3D U-net architecture, during training, the various filters within the 3D CNN and 3D de-CNN layers learn to encode meaningful features that would aid the effort of prediction accuracy. During training, matching sets of 3D image data 1122 and encoded matching 3D positional features 1160 are used to optimize towards prediction of the latter from the former. A loss function may be employed as a measure to be minimized. This optimization effort may be aided be making use of optimizers such as SGD, Adam, etc.

Such an architecture may employ various internal resolution scales, effectively downscaling 1126, 1130, 1134 as results from a previous set of 3D CNN layers 1124, 1128, 1132 through max pooling. The term 'meaningful features' here refers to (successive) derivations of information relevant to determining the target output values and are also encoded through the 3D de-CNN layers, which effectively perform an upscaling whilst employing filters. By combining 1140, 1146, 1152 data resulting from such 3D de-CNN layers 1138, 1144, 1154 with the data from the 'last' 3D CNN layers operating on the same resolution (1132 to 1140, 1128 to 1146 and 1124 to 1152), highly accurate predictions may be achieved. Throughout the upscaling path, additional 3D CNN layers may be used 1142, 1148, 1154.

When being utilized for inference, having been trained to have encoded internal parameters in such a way that validation yields sufficiently accurate results, an input sample may be presented, and the 3D deep learning network may yield predicted 3D positional features 542.

An example of a reference object for use in determination of manually engineered 3D positional features, in this case a curve that approximates a dental arch, is provided in FIG. 12. In this example, a cloud of points in the axial (xy) plane indicates areas of high intensity values (bright white areas) may indicate areas of teeth or jaw structures. In order to determine a dental arch curve, the computer may determine areas in an axial plane of the image volume associated with bright voxels (e.g. voxels having an intensity value above a predetermine threshold value) which may be identified as teeth or jaw voxels. These areas of high intensity may be used to determine a crescent arrangement of bright areas that approximates the dento-maxillofacial arch. This way, a dental arch curve may be determined, which approximates an average of the dento-maxillofacial arches of the upper jaw and the lower jaw respectively. In another embodiment, separate dental arch curves associated with the upper and low jaw may be determined.

FIG. 13A-13E depict examples of 3D positional features of 3D image data according to various embodiments of the invention.

FIG. 13A depicts (left) an image of a slice of the sagittal plane of a 3D image data stack and (right) an associated visualization of a so-called height-feature of the same slice. Such height feature may encode a z-position (a height 1304) of each voxel in the image volume of the 3D CT image data stack relative to a reference plane 1302. The reference plane (e.g. the axial or xy plane which is determined to be (the best approximation of) the xy plane with approximately equal distance to both the upper jaw and the lower jaw and their constituent teeth.

Other 3D positional features may be defined to encode spatial information in an xy space of a 3D image data stack. In an embodiment, such positional feature may be based on a curve which approximates (part of) the dental arch. Such a positional feature is illustrated in FIG. 13B, which depicts (left) a slice from an 3D image data stack and (right) a visualization of the so-called travel-feature for the same slice. This travel-feature is based on the curve that approximates the dental arch 1306 and defines the relative distance 1308 measured along the curve. Here, zero distance may be defined as the point 1310 on the curve where the derivative of the second-degree polynomial is (approximately) zero. The travelled distance increases when moving in either direction on the x-axis, from this point (e.g. the point where the derivative is zero).

A further 3D positional feature based on the dental arch curve may define the shortest (perpendicular) distance of each voxel in the image volume to the dental arch curve 1306. This positional feature may therefore be referred to as the 'distance-feature'. An example of such feature is provided in FIG. 13C, which depicts (left) a slice from the 3D image data stack and (right) a visualization of the distance-feature for the same slice. For this feature, zero distance means that the voxel is positioned on the dental arch curve 1308.

Yet a further 3D positional feature may define positional information of individual teeth. An example of such feature (which may also be referred to as a dental feature) is provided in FIG. 13D, which depicts (left) a slice from the 3D image data stack and (right) a visualization of the dental feature for the same slice. The dental feature may provide information to be used for determining the likelihood to find voxels of certain teeth at a certain position in the voxel space. This feature may, following a determined reference plane such as 1302, encode a separate sum of voxels over the normal to any plane (e.g. the x-y plane or any other plane). This information thus provides the neural network with a 'view' of all information from the original space as summed over the plane normal. This view is larger than would be processed when excluding this feature and may provide a means of differentiating whether a hard structure is present based on all information in the chosen direction of the space (as illustrated in $1312_{1,2}$ for the x-y plane).

Figure 13E:
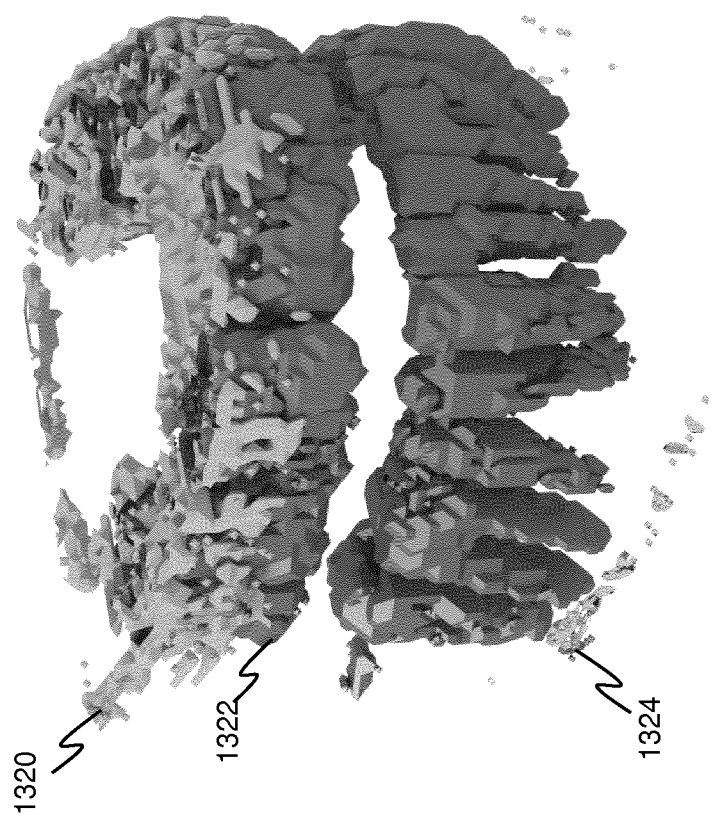

FIG. 13E shows a visualization of 3D positional features as may be generated by a machine learning pre-processor, in particular a 3D deep neural network as described with respect to FIG. 10B. These 3D positional features have been computer rendered in 3D and shown 3D volumes are the result of thresholding of predicted values. From the relative 'roughness' of the surfaces defining the volumes it can be seen that such network and it's input and target data operated on a lower 3D resolution than that of the definitive voxel representation to be segmented (In the case of this example, a resolution of 1×1×1 mm per voxel was employed). As targets, the same training data might be used as might have been employed for the segmentation 3D deep learning network, but down-sampled to an applicable resolution that adheres to processing requirements for usage by such a pre-processing 3D deep neural network. This leads to, in effect, such 3D positional features containing a 'rough' pre-segmentation of, in the case of this example, jaw 1320, tooth 1322 and nerve 1324 structures. For the purpose of this illustration, the lower jaw of this particular patient has not been rendered so as to show the voxels classified as being most likely to be part of the nerve structure.

Such rough pre-segmentation may be appropriately up-sampled, e.g. by means of interpolation, ensuring that per voxel at the desired segmentation resolution (being the originally received voxel resolution), information from such pre-segmentation spatially coincides at the desired resolution. For example, information from one voxel in the shown visualization may spatially coincide with 5×5×5 voxels at the desired resolution, and this information should be paired with all applicable 125 voxels at the desired resolution. Afterwards this up-sampled information may be presented as, or included in, a set of 3D positional features and, as described with reference to FIGS. 10A and 10B be fed into the segmentation 3D deep neural network as input.

Figure 14C:
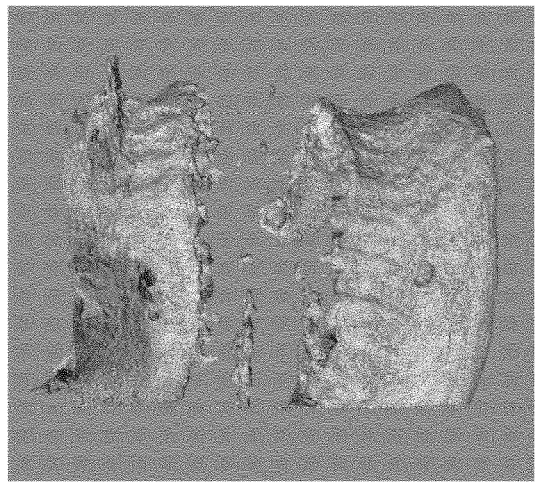
FIG. 14A-14D depict examples of the output of a trained deep learning neural network according to an embodiment of the invention.
Figure 14D:
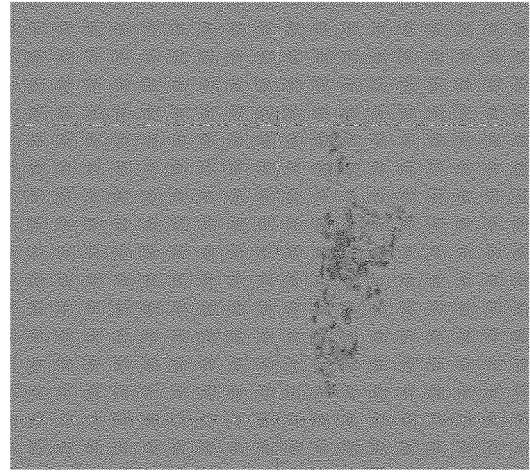
Figure 14A:
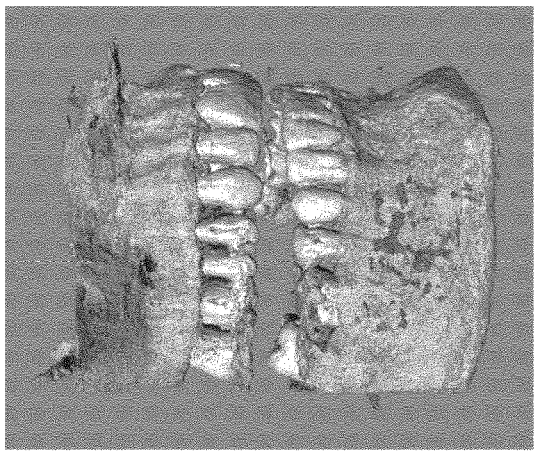
Figure 14B:
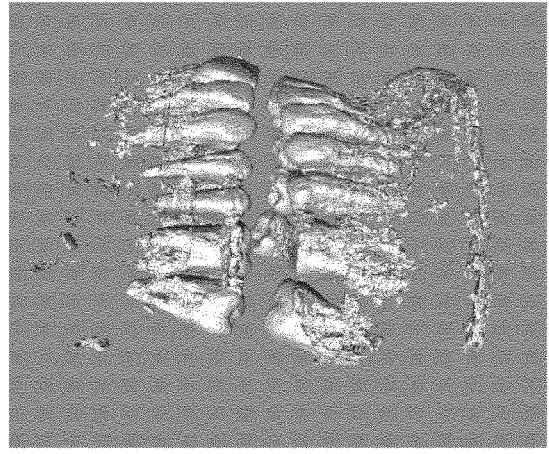

FIG. 14A-14D depict examples of the output of a trained deep learning neural network according to an embodiment of the invention. In particular, FIG. 14A-14D depict 3D images of voxels that are classified using a deep learning neural network that is trained using a training method as described with reference to FIG. 8. As shown in FIGS. 14B and 14C, voxels may be classified by the neural network in voxels belonging to teeth structures (FIG. 14B), jaw structures (FIG. 14C) or nerve structures (FIG. 14D). FIG. 14A depicts a 3D image including the voxels that the deep learning neural network has classified as teeth, jaw and nerve tissue. As shown by FIG. 14B-14D, the classification process is accurate but there are still quite a number of voxels that are missed or that are wrongly classified. For example, as shown in FIGS. 14B and 14C voxels that may be part of the jaw structure are classified as teeth voxels while in the surfaces belonging to the roots of the teeth voxels are missed. As shown in FIG. 14D, this problem is even more pronounced with classified nerve voxels.

Figure 15:
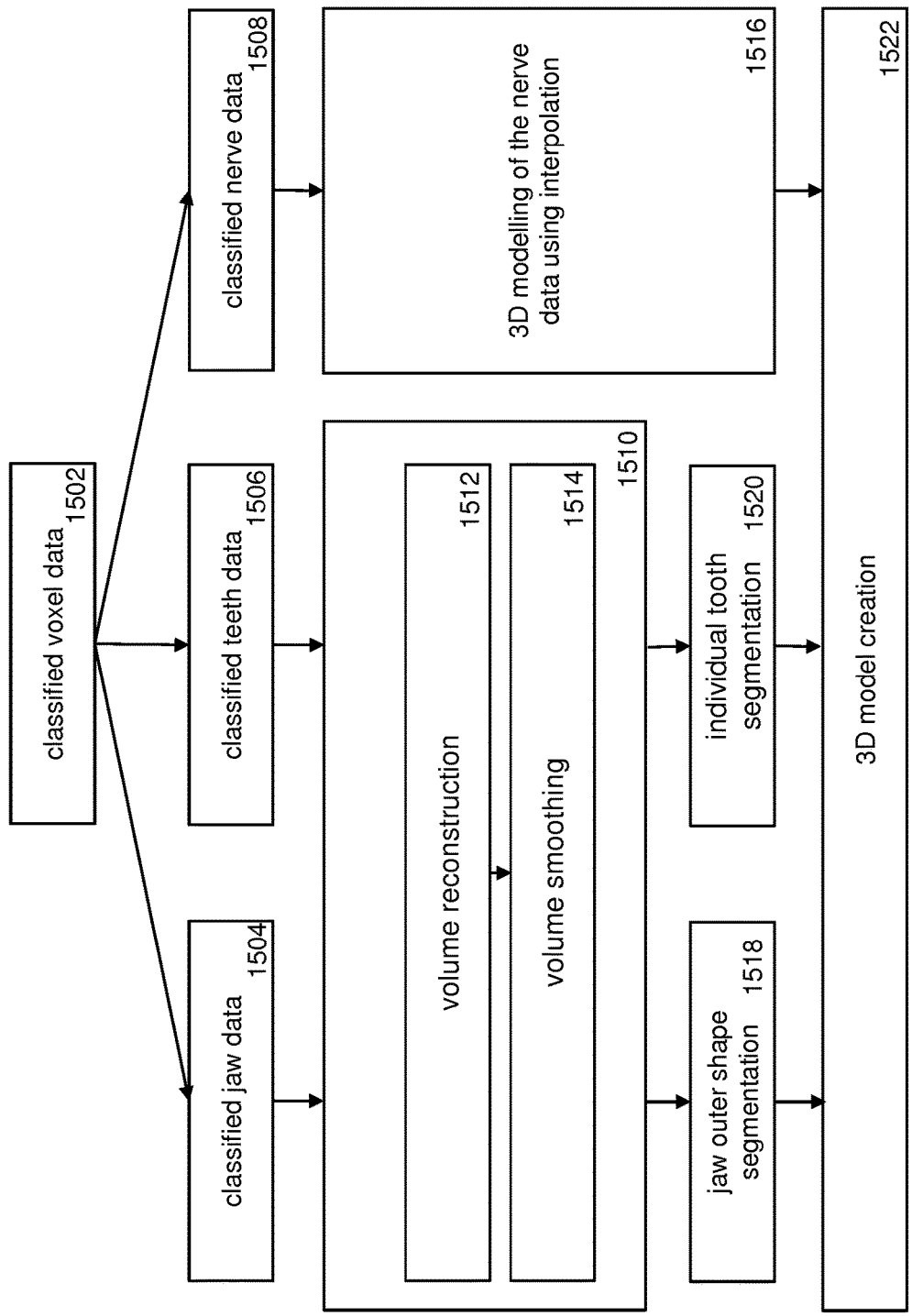
FIG. 15 depicts a flow-diagram of post-processing classified voxels of 3D dento-maxillofacial structures according to an embodiment of the invention.

In order to address the problem of outliers in the classified voxels (which form the output of the first deep learning neural network), the voxels may be post-processed. FIG. 15 depicts a flow-diagram of post-processing classified voxels of 3D dento-maxillofacial structures according to an embodiment of the invention. In particular, FIG. 15 depicts a flow diagram of post-processing voxel data of dento-maxillofacial structures that are classified using a deep learning neural network as described with reference to FIG. 7-14 of this application.

As shown in FIG. 15 the process may include a step of dividing the classified voxel data 1502 of 3D dento-maxillofacial structure into voxels that are classified as jaw voxels 1504, teeth voxels 1506 and voxels that are classified as nerve data 1508. As will be described hereunder in more detail, the jaw and teeth voxels may be post-processed using a further, second deep learning neural network 1510. In contrast to the initial first deep learning neural network (which uses a 3D CT image data stack of a dento-maxillofacial structure and associated positional features as input), which generates the best possible voxel classification based on the image data, the second 'post processing' deep learning neural network translates parts of the output of the first deep learning neural network to voxels so that the output more closely matches the desired 3D structures.

The post-processing deep learning neural network encodes representations of both teeth and jaw. During the training of the post-processing deep learning neural network, the parameters of the neural network are tuned such that the output of the first deep learning neural network is translated to the most feasible 3D representation of these dento-maxillofacial structures. This way, imperfections in the classified voxels can be reconstructed 1512. Additionally, the surface of the 3D structures can be smoothed 1514 so that the most feasible 3D jaw model and teeth models can be generated. Omitting the 3D CT image data stack from being an information source for the post processing neural network makes this post processing step robust against undesired variances within the image stack.

Due to the nature of the (CB)CT images, the output of the first deep learning neural network will suffer from (before mentioned) potential artefacts such as averaging due to patient motion, beam hardening, etc. Another source of noise is variance in image data captured by different CT scanners. This variance results in various factors being introduced such as varying amounts of noise within the image stack, varying voxel intensity values representing the same (real world) density, and potentially others. The effects that the above-mentioned artefacts and noise sources have on the output of the first deep learning neural network may be removed or at least substantially reduced by the post-processing deep learning neural network, leading to segmented jaw voxels and segmented teeth voxels.

The segmented teeth voxels may consist of all voxels that may be considered to be part of any tooth, and thus may contain representations of all teeth present in a dentition. A process may be applied to the total set of teeth voxels in order to separate the teeth voxels into sets of voxels belonging to individual teeth 1520. In such a process, regions of connected voxels may be considered as individual objects and maybe be split into separate representations of individual teeth.

Individual teeth voxels may be connected, and additional processing may be employed in order to split all volumes to be considered as individual teeth. This may be done employing known methods from the fields of image processing and morphology, in particular by employing watershedding and erosion.

In more detail, the expected volume of an individual tooth may be used to iteratively perform a number of steps until all sets of split voxels match the expected volume of a tooth. Performing successive 3D erosion steps on the teeth voxels may separate previously connected sets of voxels. Coordinates of the centres of these (newly) separated regions may be used as starting points for 3D watershedding of the (original) teeth voxels, which may yield separate sets of voxels whilst being connected. Iteratively performing erosion until sets of voxels are separated, performing watershedding as described above, and checking whether minimum and maximum volume conditions are met, may yield sets of voxels that meet the requirements consistent with being an individual tooth.

The classified nerve data 1508 may be post-processed separately from the jaw and teeth data. The nature of the nerve data, which represent long thin filament structures in the CT image data stack, makes this data less suitable for post-processing by a deep learning neural network. Instead, the classified nerve data is post-processed using an interpolation algorithm in order to procedure segmented nerve data 1516. To that end, voxels that are classified as nerve voxels and that are associated with a high probability (e.g. a probability of 95% or more) are used by the fitting algorithm in order to construct a 3D model of the nerve structures. Thereafter, the 3D jaw, teeth and nerve models are combined into a 3D model of the dento-maxillofacial structure.

Figure 16:
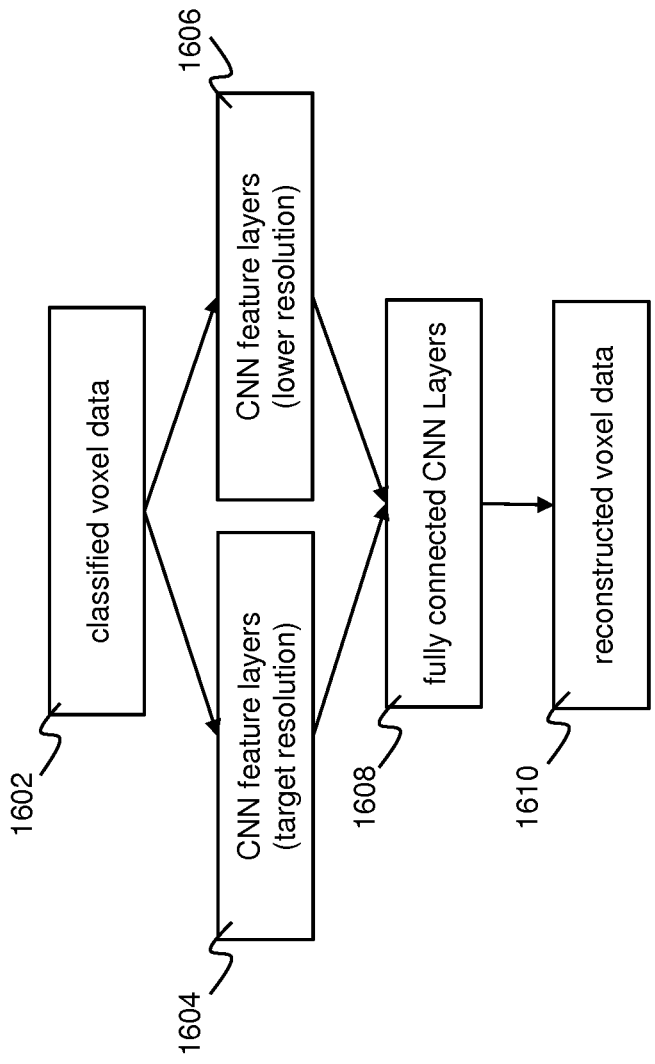
FIG. 16 depicts a deep neural network architecture for post-processing classified voxels of 3D dento-maxillofacial structures according to an embodiment of the invention.

FIG. 16 depicts an example of an architecture of a deep learning neural network that is configured for post-processing classified voxels of a 3D dento-maxillofacial structure according to an embodiment of the invention. The post-processing deep learning neural network may have an architecture that is similar to the first deep learning neural network, including a first path formed by a first set of 3D CNN feature layers 1604, which is configured to process the input data (in this case a part of classified voxel data) at the resolution of the target. The deep learning neural network further includes a second set of 3D CNN feature layers 1606, which is configured to process the context of the input data that are processed by the first 3D CNN feature layers but then at a lower resolution than the target. The output of the first and second 3D CNN feature layers are then fed to the input of a set of fully connected 3D CNN layers 1608 in order to reconstruct the classified voxel data such that they closely represent a 3D model of the 3D dento-maxillofacial structure. The output of the fully connected 3D CNN layer provides the reconstructed voxel data.

The post-processing neural network may be trained using the same targets as first deep learning neural network, which represent the same desired output. During training, the network is made as broadly applicable as possible by providing noise to the inputs to represent exceptional cases to be regularized. Inherent to the nature of the post-processing deep learning neural network, the processing it performs also results in the removal of non-feasible aspects from the received voxel data. Factors here include the smoothing and filling of desired dento-maxillofacial structures, and the outright removal of non-feasible voxel data.

Figure 17B:
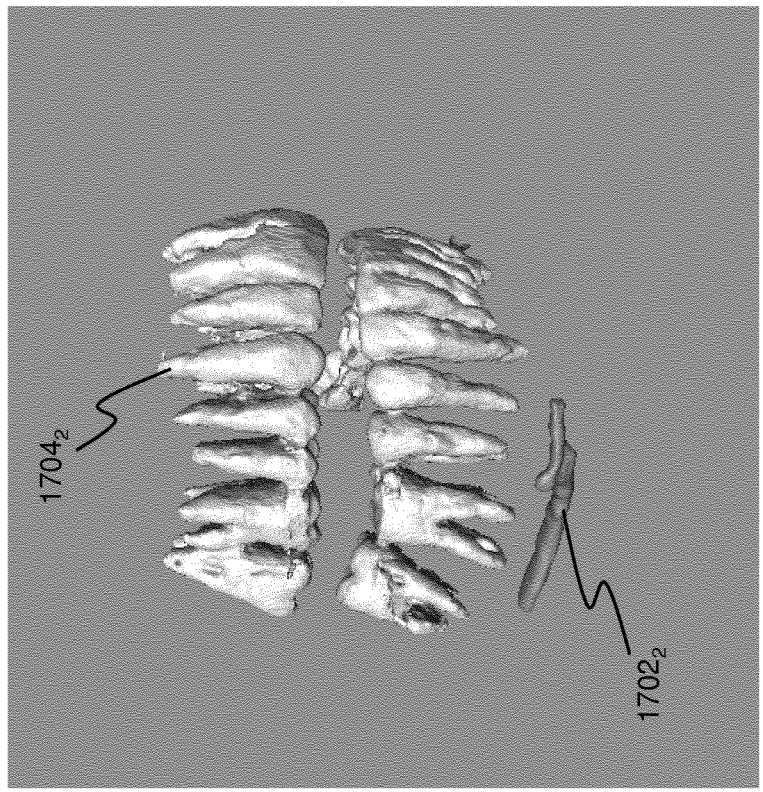
FIG. 17A-17B depict a surface reconstruction process of classified voxels according to an embodiment of the invention.
Figure 17A:
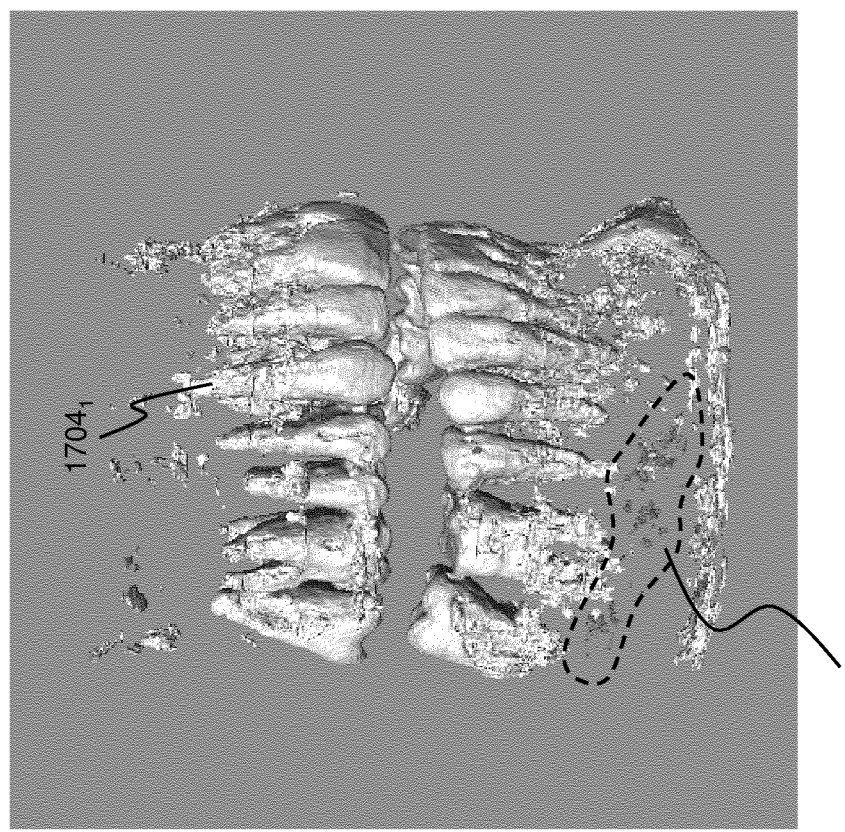

FIGS. 17A and 17B depicts an iteration of the post-processing network resulting in surface reconstruction of classified voxels according to an embodiment of the invention. In particular, FIG. 17A depicts a picture of classified voxels of teeth structures, wherein the voxels are the output of the first deep learning neural network. As shown in the figure noise and other artefacts in the input data result in irregularities and artefacts in the voxel classification and hence 3D surface structures that include gaps in sets of voxels that represent a tooth structure. These irregularities and artefacts are especially visible at the inferior alveolar nerve structure $1702_1$, and the dental root structures $1704_1$ of the teeth, i.e. the areas where the deep learning neural network has to distinguish between teeth voxels and voxels that are part of the jaw bone.

FIG. 17B depicts the result of the post-processing according the process as described with reference to FIGS. 15 and 16. As shown in this figure the post-processing deep learning neural network successfully removes artefacts that were present in the input data (the classified voxels). The post-processing step successfully reconstructs parts that were substantially affected by the irregularities and artefacts, such as the root structures $1704_1$ of the teeth which now exhibit smooth surfaces that provide an accurate 3D model of the individual tooth structures $1704_2$. High probability nerve voxels $1702_1$ (e.g. a probability of 95% or more) are used by a fitting algorithm in order to construct a 3D model of the nerve structures $1702_2$.

Figure 18:
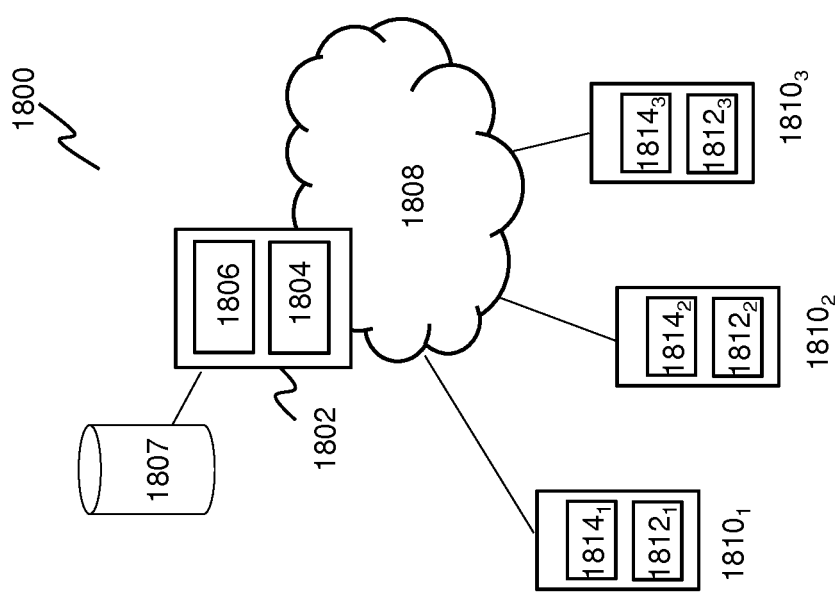
FIG. 18 depicts a schematic of a distributed computer system for processing 3D data according to various embodiments of the invention.

FIG. 18 depicts a schematic of a distributed computer system according to an embodiment of the invention. The distributed computer system may be configured to process the 3D data on the basis of the trained 3D deep learning processors as described in this application and for rendering the processed 3D data. As shown in FIG. 18, the trained 3D deep learning processors may be part of a distributed system comprising one or more servers 1802 in the network and multiple terminals $1810_{1-3}$, preferably mobile terminals, e.g. a desktop computer, a laptop, an electronic tablet, etc. The (trained) 3D deep learning processors may be implemented as server applications 1804, 1806. Further, a client application (a client device) $1812_{1-3}$ executed on the terminals may include a user interface enabling a user to interact with the system and a network interface enabling the client devices to communicate via one or more networks 1808, e.g. the Internet, with the server applications. A client device may be configured to receive input data. The client device may transmit the data to the server application, which may process the data on the basis of the methods and systems as described in this application. The processed data may be sent back to the client device and a rendering engine $1814_{1-3}$ associated with the client device may use the resulting 3D image data to render the 3D tooth models. In another embodiment, part or the data processing may be executed at the client side. For example, any pre-processing and/or post-processing described in this disclosure may be executed by the client device. In further embodiments, instead of a distributed computer system, a central computer system may be used to execute any processing described in this application.

Hence, as shown by FIG. 18, the invention provides a fully automated pipeline for the prediction of root shapes on the basis of 3D data representing a crow. A user may provide 3D image data, e.g. (CB)CT 3D data or an intra-oral scan, representing a dento-maxillofacial structure or a dentition, to the input of the system and in response the system will generate root shape(s) to match crowns as represented in the source data, which can be presented to the user in different graphical formats, e.g. as a 3D rendering or as mark-up in displayed image slices. The input data are automatically optimized for input to the 3D deep neural network so that the 3D deep neural network is capable of accurately processing the 3D image data without any human intervention. Moreover, the invention allows 3D rendering of output generated by the 3D deep neural network processors, i.e. full teeth containing the predicted root. Such visual information is indispensable for state of the art dental applications in dental care and dental reporting, orthodontics, orthognathic surgery, forensics, biometrics, etc.

Figure 19:
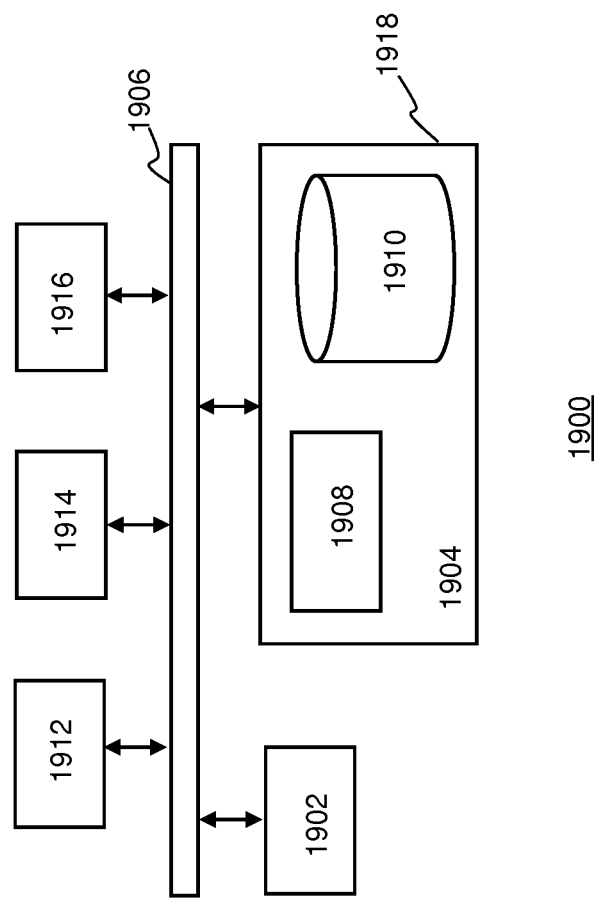
FIG. 19 is a block diagram illustrating an exemplary data computing system that may be used for executing methods and software products described in this disclosure.

FIG. 19 is a block diagram illustrating exemplary data processing systems described in this disclosure. Data processing system 1900 may include at least one processor 1902 coupled to memory elements 1904 through a system bus 1906. As such, the data processing system may store program code within memory elements 1904. Further, processor 1902 may execute the program code accessed from memory elements 1904 via system bus 1906. In one aspect, data processing system may be implemented as a computer that is suitable for storing and/or executing program code. It should be appreciated, however, that data processing system 1900 may be implemented in the form of any system including a processor and memory that is capable of performing the functions described within this specification.

Memory elements 1904 may include one or more physical memory devices such as, for example, local memory 1908 and one or more bulk storage devices 1910. Local memory may refer to random access memory or other non-persistent memory device(s) generally used during actual execution of the program code. A bulk storage device may be implemented as a hard drive or other persistent data storage device. The processing system 1900 may also include one or more cache memories (not shown) that provide temporary storage of at least some program code in order to reduce the number of times program code must be retrieved from bulk storage device 1910 during execution.

Input/output (I/O) devices depicted as input device 1912 and output device 1914 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 1916 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 1900.

As pictured in FIG. 19, memory elements 1904 may store an application 1918. It should be appreciated that data processing system 2100 may further execute an operating system (not shown) that can facilitate execution of the application. Application, being implemented in the form of executable program code, can be executed by data processing system 1900, e.g., by processor 1902. Responsive to executing application, data processing system may be configured to perform one or more operations to be described herein in further detail. In one aspect, for example, data processing system 1900 may represent a client data processing system. In that case, application 1918 may represent a client application that, when executed, configures data processing system 1900 to perform the various functions described herein with reference to a "client". Examples of a client can include, but are not limited to, a personal computer, a portable computer, a mobile phone, or the like. In another aspect, data processing system may represent a server. For example, data processing system may represent an (HTTP) server in which case application 1918, when executed, may configure data processing system to perform (HTTP) server operations. In another aspect, data processing system may represent a module, unit or function as referred to in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Figure 20A:
FIG. 20 shows a representation of visualisations of 3D tooth models towards an end-user according to an embodiment of the invention.
Figure 20B:
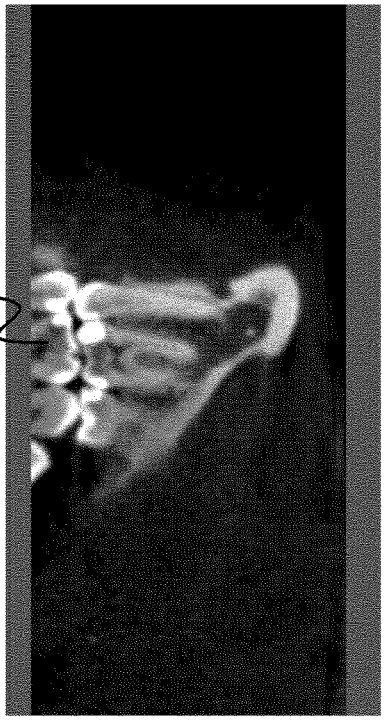
Figure 20C:
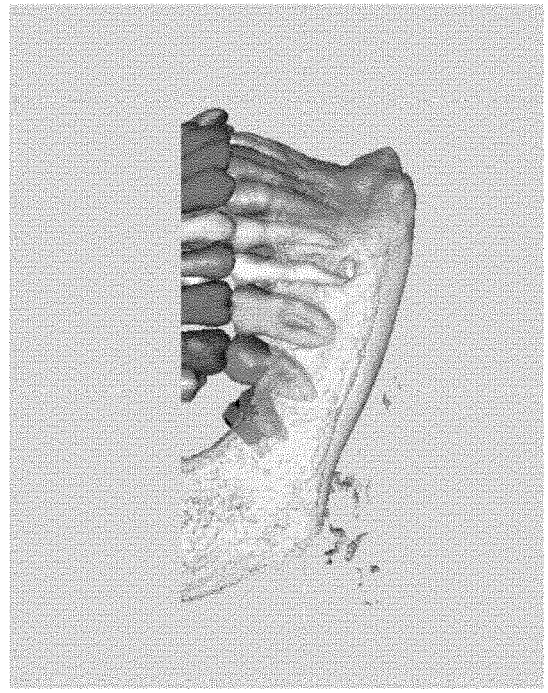
Figure 20D:
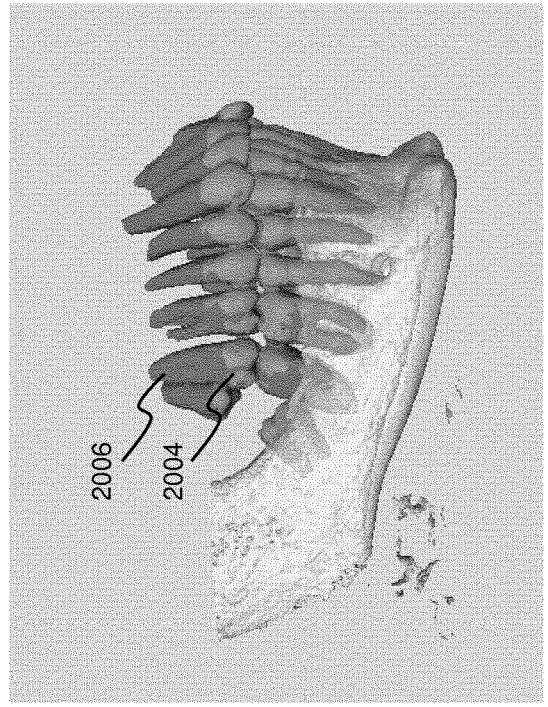

FIG. 20A to FIG. 20D show a representation of visualisations of 3D tooth models towards an end-user according to an embodiment of the invention. FIG. 20A and FIG. 20B show slices of 3D image data, as received by the system. These 3D data may be generated by a CBCT scanner, in respectively the coronal and sagittal plane. Both figures show the entire extent of the received data, and as can be seen the 'top-side' of the data does not contain the full teeth present within the upper jaw. The data does contain parts of crowns of teeth, which can be segmented according to the methods as described with respect to system step 104 and detailed in FIG. 8 to FIG. 17, resulting in the 3D model representation of the dento-maxillofacial structures as shown in FIG. 20C, more specifically the individual (in some cases partial) teeth and jaw structures. After pre-processing the 3D data using e.g. a method as described with reference to FIG. 4, a voxel representations of the incomplete crown models may be individually passed to the trained 3D deep neural network 106 to obtain the root shape prediction as illustrated in FIG. 20D by individual crown 2004 (2002 as indicated in the source data) and predicted individual root 2006.

The system may automatically perform this process for all individual tooth entities considered as being crowns and incomplete, which may be determined e.g. by making use of known information considering complete teeth such as expected minimum real-world dimensions of the volume considered to be (part of a) tooth, and an expected maximum change in the surface area considered to be part of a tooth, the surface area being within a plane intersecting the model, and the change in area being the result of iteratively moving a normal plane along the 'up-down' (in the real-world co-ordinate system) axis with a set step-size. In other words, scanning the volume of the (part of a) tooth along the up-down axis may yield any abrupt changes/termination of the volume indicating that the tooth is yet incomplete.

After generation of predictions for all applicable crown sections, post-processor 108 may result in 3D image data 110 as visually represented by FIG. 20D, providing an end-user complete teeth with predicted root-sections based on received crown-sections for 3D image data.

The invention claimed is:

1. A computer-implemented method for automated 3D root shape prediction comprising:
   a pre-processor receiving 3D data defined in a voxel space, the voxel space defining a 3D volume, the voxel space comprising a voxel representation of a crown, and processing the voxel representation such that it is in a scale, position and orientation that corresponds to voxel representations that are used to train a first 3D deep neural network;
   the pre-processor providing the voxel representation of the crown to the input of the first 3D deep neural network, the first 3D deep neural network being trained on the basis of a training set of pre-processed clinical 3D data defining 3D representations of real teeth, the trained deep neural network being configured to predict an anatomically accurate voxel representation of a root corresponding to the crown or a voxel representation of a complete tooth;
   the first 3D deep neural network generating a voxel representation of a predicted root or of a complete tooth comprising the predicted root on the basis of the voxel representation of the crown, wherein the generation of the voxel representation of the predicted root or the complete tooth includes:
   determining voxel activations for voxels in a voxel space of the output of the first 3D deep learning network, each voxel activation representing a probability measure defining the probability that a voxel is at least part of the root or of the complete tooth; and,
   determining whether a voxel activation is part of the root or of the complete tooth by comparing the voxel activation with a voxel activation threshold value.

2. The method according to claim 1 further comprising:
   a post-processor receiving the voxel representation of the predicted root generated by the first 3D deep neural network and processing the voxel representation of the predicted root and the 3D crown, the processing including:

merging the voxels of the 3D root and the 3D crown into a voxel representation of a complete 3D tooth.

3. The method according to claim 2 wherein the processing includes transforming the voxel representation of the complete 3D tooth in a 3D mesh of a complete tooth.

4. The method according to claim 1 wherein the 3D data defines a 3D representation of at least part of a dentition, the processing by the pre-processor further including:
segmenting the 3D data into at least one 3D data set, the 3D data set representing a 3D crown of a tooth of the dentition; and,
transforming the 3D data set into a voxel representation of the crown, the voxel representation matching the voxel space of the input of the first 3D deep neural network.

5. The method according to claim 1 wherein the 3D data received by the pre-processor are 3D data generated by an optical scanner, the 3D data defining a 3D surface mesh representing at least part of a dentition comprising a plurality of crowns, wherein the processing by the pre-processor further includes:
segmenting the 3D mesh into a plurality of segmented 3D meshes wherein each segmented 3D mesh represents a 3D crown of the dentition;
transforming each segmented 3D surface mesh into a voxel representation of the crown, the voxel representation matching the voxel space of the input of the first 3D deep neural network.

6. The method according to claim 1 wherein the 3D data received by the pre-processor are generated by an X-ray scanner, the 3D data defining a voxel representation of at least part of a dento-maxillofacial structure, the dento-maxillofacial structure including a plurality of teeth of at least part of a dentition, wherein the processing by the pre-processor further includes:
classifying at least part of the voxels representing the dento-maxillofacial structure into at least one of jaw, teeth and/or nerve voxels using a second 3D deep neural network; the second 3D deep neural network being trained on the basis of 3D image data of dento-maxillofacial structures; and,
segmenting the classified voxels into one or more 3D data sets, each of the one or more 3D data sets defining a voxel representation of a tooth in the dentition of the dento-maxillofacial structure.

7. The method according to claim 6 wherein the processing by the pre-processor further includes:
providing a further voxel representation of the dento-maxillofacial structure to the input of a third 3D deep neural network, the third deep neural network being trained to determine for each voxel of the voxel representation at the input at least one 3D positional feature, a 3D positional feature including a measure indicating a likelihood that a voxel represents jaw, teeth and/or nerve tissue, wherein the further voxel representation of the dento-maxillofacial structure is a low-resolution version of the voxel representation of the dento-maxillofacial structure;
providing the one or more 3D positional features and the voxel representation of the dento-maxillofacial structure to the second 3D deep neural network and the second 3D deep neural network using the one or more positional features to classify at least part of the voxels in the voxel space into at least one of jaw, teeth and/or nerve voxels.

8. The method of claim 7 wherein the resolution of the further voxel representation is at least three times lower than the resolution of the first voxel presentation.

9. The method of claim 8 wherein the third 3D deep neural network is trained based on the 3D image data of dento-maxillofacial structures and the one or more 3D models of parts of the dento-maxillofacial structures of the 3D image data of the training set for training the second deep neural network.

10. The method according to claim 6 wherein the second deep neural network comprises a plurality of first 3D convolutional layers, the output of the plurality of first 3D convolutional layers being connected to at least one fully connected layer, wherein the plurality of first 3D convolutional layers are configured to process a first block of voxels from the first voxel representation and wherein the at least one fully connected layer is configured to classify voxels of the first block of voxels into at least one of jaw, teeth and/or nerve voxels.

11. The method according to claim 10 wherein the second deep neural network further comprising a plurality of second 3D convolutional layers, the output of the plurality of second 3D convolutional layers being connected to the at least one fully connected layer, wherein the plurality of second 3D convolutional layers are configured to process a second block of voxel from the first voxel representation, the first and second block of voxels having the same or substantially the same centre point in the image volume and the second block of voxels representing a volume in read-world dimensions that is larger than the volume in real-world dimensions of the first block of voxels, the plurality of second 3D convolutional layers being configured to determine contextual information associated with voxels of the first block of voxels that is provided to the input of the plurality of first 3D convolutional layers.

12. The method according to claim 6 wherein classifying uses one or more 3D positional features derived from the 3D image data of the training set, and one or more 3D models of parts of the dento-maxillofacial structures of the 3D image data of the training set, the one or more 3D models being used as target during training of the first deep neural network.

13. The method according to claim 1 wherein the first 3D deep neural network includes a plurality of 3D convolutional layers connected via one or more densely connected layers to a plurality of 3D deconvolutional layers and wherein the first deep neural network is trained on the basis of voxel representations of crowns and associated roots or on the basis of voxel representations of crowns and associated teeth.

14. The method of claim 13 wherein the first 3D deep neural network at at least a plurality of 3D convolutional layers is configured such that the spatial resolution of derived information resulting from the section is reduced compared to the input resolution, one or more layers configured to process information resulting from the at least a plurality of 3D convolutional layers in parallel.

15. The method of claim 14 wherein the one or more layers comprises one or more densely connected layers, and at least a plurality of 3D convolutional layers is configured such that the spatial resolution of the resulting output of the total network is at least of the same resolution as the input resolution.

16. The method of claim 15 wherein the first 3D deep neural network has an 3D U-net type deep neural network architecture, at least part of the voxel representations being derived from segmented 3D X-ray data, representing one or more dento-maxillofacial structures.

17. The method according to claim 1 further comprising:
a post-processor receiving the voxel representation of the predicted root generated by the first 3D deep neural network and processing the voxel representation of the predicted root and the 3D crown, the processing including:
merging the voxels of the 3D root and the 3D crown into a voxel representation of a complete 3D tooth; and, optionally,
transforming the voxel representation of the complete 3D tooth in a 3D mesh of a complete tooth.

18. A computer-implemented method for training a 3D deep learning neural network to generate a prediction of 3D root shape comprising:
a computer receiving training data, the training data including clinical 3D data comprising voxel representations of crowns and associated roots or on the basis of voxel representations of crowns and associated teeth wherein at least part of the voxel representations being derived from segmented 3D X-ray data; and/or, derived from optically scanned complete teeth;
offering a voxel representation of a crown to the input of the 3D deep neural network and the 3D deep neural network generating a voxel representation of a predicted root;
optimizing values of one or more network parameters of the 3D deep neural network by minimizing a loss function representing a deviation between the voxel representation of a predicted root or a predicted complete tooth and the voxel representation of a root or a complete tooth that is associated with the voxel representation of the crown that was offered to the input of the 3D deep neural network; and,
storing the optimized values in a computer readable storage medium, the optimized values defining one or more network parameters of a trained neural network configured to, when provided with a voxel representation of a crown, predict an anatomically accurate voxel representation of a root corresponding to the crown or a voxel representation of a complete tooth.

19. The method according to claim 18 wherein the 3D deep neural network includes a plurality of 3D convolutional layers connected via one or more densely connected layers to a plurality of 3D deconvolutional layers.

20. A computer system adapted to automatically predict a 3D root shape comprising:
a computer readable storage medium having computer readable program code embodied therewith, the program code including a pre-processing algorithm and at least a trained 3D deep neural network; and a processor coupled to the computer readable storage medium, wherein responsive to executing the computer readable program code, the processor is configured to perform executable operations comprising:
a pre-processor receiving 3D data defined in a voxel space, the voxel space defining a 3D volume, the voxel space comprising a voxel representation of a crown, and processing the voxel representation such that it is in a scale, position and orientation that corresponds to voxel representations that are used to train a first 3D deep neural network;
the pre-processor providing the voxel representation of the crown to the input of the first 3D deep neural network, the first 3D deep neural network being trained on the basis of a training set of pre-processed clinical 3D data defining 3D representations of real teeth, the trained deep neural network being configured to predict an anatomically accurate voxel representation of a root corresponding to the crown or a voxel representation of a complete tooth;
the first 3D deep neural network generating a voxel representation of a predicted root or of a complete tooth comprising the predicted root on the basis of the voxel representation of the crown, wherein the generation of the voxel representation of the predicted root or the complete tooth includes:
determining voxel activations for voxels in a voxel space of the output of the first 3D deep learning network, each voxel activation representing a probability measure defining the probability that a voxel is part of the root or of the complete tooth; and,
determining whether a voxel activation is part of the root or of the complete tooth by comparing the voxel activation with a voxel activation threshold value.

* * * * *